(12) United States Patent
Caldwell et al.

(10) Patent No.: US 6,211,134 B1
(45) Date of Patent: Apr. 3, 2001

(54) MUTANT α-AMYLASE

(75) Inventors: Robert M. Caldwell, San Carlos; Colin Mitchinson, Half Moon Bay; Traci H Ropp, San Francisco, all of CA (US)

(73) Assignee: Genecor International, Inc., Rochester, NY (US)

( * ) Notice: Subject to any disclaimer, the term of this patent is extended or adjusted under 35 U.S.C. 154(b) by 0 days.

(21) Appl. No.: 08/985,659

(22) Filed: Dec. 9, 1997

Related U.S. Application Data

(63) Continuation-in-part of application No. 08/645,971, filed on May 14, 1996, now Pat. No. 5,763,385.

(51) Int. Cl.[7] .............................. C11D 3/386; C12N 9/26; C12N 15/00
(52) U.S. Cl. .................... 510/392; 510/321; 510/330; 510/226
(58) Field of Search .................... 435/201, 202, 435/203; 510/392, 530, 320, 321, 226

(56) References Cited

U.S. PATENT DOCUMENTS

| | | | |
|---|---|---|---|
| 5,736,499 | * | 4/1998 | Mitchinson et al. ............... 510/392 |
| 5,753,460 | * | 5/1998 | Bisgård-Frantzen et al. ...... 455/69.1 |
| 5,763,385 | * | 6/1998 | Bott et al. ........................... 510/392 |
| 5,801,043 | * | 9/1998 | Bisgård-Frantzen et al. .... 435/256.3 |
| 5,824,532 | * | 10/1998 | Barnett et al. ...................... 455/262 |
| 5,830,837 | * | 11/1998 | Bisgård-Frantzen et al. ...... 510/226 |
| 5,989,169 | * | 11/1999 | Svendsen et al. .................. 485/201 |
| 6,022,724 | * | 11/1999 | Svendsen et al. .................. 435/202 |

* cited by examiner

Primary Examiner—Kery Fries
(74) Attorney, Agent, or Firm—Christopher L. Stone

(57) ABSTRACT

Novel α-amylase enzymes are disclosed having a substution equivalent to G475R in *Bacillus licheniformis*. The disclosed α-amylase enzymes show improved specific activity and starch hydrolysis performance. Also provided are polynucleotides encoding such enzymes, expression vectors including such polynucleotides, host cells transformed with such expression vectors, and the use of such enzymes in detergent compositions.

17 Claims, 14 Drawing Sheets

N188T 5'-G GAT TGG GAA GTG TCG ACT GAA AAC GGC AAC TAT GAT-3' (SEQ ID NO:4)
                                    SalI

N188P 5'-G GAT TGG GAA GTT TCC CCA GAA AAT GGC AAC TAT GAT-3' (SEQ ID NO:5)
                                        pflMI N188R 5'-G GAT TGG GAA GTT TCT AGA GAA AAC GGC AAC TAT GAT-3' (SEQ ID NO:6)
                                    XbaI N188L 5'-G GAT TGG GAA GTT TCC CTC GAG AAC GGC AAC TAT GAT-3' (SEQ ID NO:7)
                                        XhoI N188A 5'-G GAT TGG GAA GTT TCG GCC GAA AAC GGC AAC TAT GAT-3' (SEQ ID NO:8)
                                    EagI N188G 5'-G GAT TGG GAA GTT TCC GGA GAA AAC GGC AAC TAT GAT-3' (SEQ ID NO:9)
                                    BspEI N188V 5'-G GAT TGG GAA GTT AGC GTC GAA AAC GGC AAC TAT GAT-3' (SEQ ID NO:10)
                                    HgaI N188K 5'-G GAT TGG GAA GTT TCC AAG GAA AAC GGC AAC TAT GAT-3' (SEQ ID NO:11)
                                    StyI N188Q 5'-G GAT TGG GAA GTT TCC CAG GAA AAT GGC AAC TAT GAT-3' (SEQ ID NO:12)
                                        BstXI N188H 5'-G GAT TGG GAA GTT TCT CAT GAA AAC GGC AAC TAT GAT-3' (SEQ ID NO:13)
                                    BspHI

FIG._1A

N188E 5'-G GAT TGG GAA GTT TCC GAA GAG AAC GGC AAC TAT GAT-3' (SEQ ID NO:14)
                                        EarI

N188D 5'-G GAT TGG GAA GTT TCC GAG GAG AAC GGC AAC TAT GAT-3' (SEQ ID NO:15)
                                        BseRI

N188Y 5'-G GAT TGG GAA GTT TCA TAT GAA AAC GGC AAC TAT GAT-3' (SEQ ID NO:16)
                                        NdeI

N188C 5'-G GAT TGG GAA GTC TCC TGC GAA AAC GGC AAC TAT GAT-3' (SEQ ID NO:17)
                            BsmAI

N188F 5'-G GAT TGG GAA GTT TCC TTC GAA AAC GGC AAC TAT GAT-3' (SEQ ID NO:18)
                                        BstBI

N188I 5'-G GAT TGG GAA GTT TCG ATC GAA AAC GGC AAC TAT GAT-3' (SEQ ID NO:19)
                                    PvuI

N188M 5'-G GAT TGG GAA GTT TCC ATG GAA AAC GGC AAC TAT GAT-3' (SEQ ID NO:20)

N188w 5'-G GAT TGG GAA GTT TCC TGG GAA AAC GGC AAC TAT GAT-3' (SEQ ID NO:21)
                                        BstNI

N188S 5'-G GAT TGG GAA GTG AGC TCT GAA AAC GGC AAC TAT GAT-3' (SEQ ID NO:22)
                                    SstI

FIG._1B

| | | |
|---|---|---|
| PCR A+ | 5'-AGG AAA GGC TTG GGA TTG GGA AGT-3' (179) | (SEQ ID NO:23) |
| PCR A− | 5'-ACT TCC CAA TCC CAA GCC TTT CCT-3' (179) | (SEQ ID NO:24) |
| PCR B+ | 5'-GGC AAC TAT GAT TAT TTG ATG TAT-3' (191) | (SEQ ID NO:25) |
| PCR B− | 5'-ATA CAT CAA ATA ATC ATA GTT GCC-3' (191) | (SEQ ID NO:26) |
| PCR LAAfs5 | 5'-CTT CAT TCC CGC GAC ATT AAC-3' (90) | (SEQ ID NO:27) |
| PCR ClaI-SalI | 5'-GA TTC CCT TGT GAG AAT AAA AG-3' (356) | (SEQ ID NO:28) |
| PCR I+ | 5'-AAT CAT GTC AGG GAA AAA ACT GGG-3' (246) <br> Bsrl | (SEQ ID NO:29) |
| PCR I− | 5'-CCC AGT TTT TTC CCT GAC ATG ATT-3' (246) <br> Bsrl | (SEQ ID NO:30) |
| PCR J+ | 5'-TTT ACG GTA GCT GAA TAT TGG CAG-3' (257) | (SEQ ID NO:31) |
| PCR J− | 5'-CTG CCA ATA TTC AGC TAC CGT AAA-3' (257) | (SEQ ID NO:32) |

FIG._2

```
AGCTTGAAGA AGTGAAGAAG CAGAGAGGCT ATTGAATAAA TGAGTAGAAA GCGCCATATC    60

GGCGCTTTTC TTTTGGAAGA AAATATAGGG AAAATGGTAC TTGTTAAAAA TTCGGAATAT   120

TTATACAACA TCATATGTTT CACATTGAAA GGGGAGGAGA ATCATGAAAC AACAAAAACG   180
                                            M  K  Q    Q  K  R

GCTTTACGCC CGATTGCTGA CGCTGTTATT TGCGCTCATC TTCTTGCTGC CTCATTCTGC   240
 L  Y  A    R  L  L  T   L  L  F    A  L  I    F  L  L  P    H  S  A

AGCAGCGGCG GCAAATCTTA ATGGGACGCT GATGCAGTAT TTTGAATGGT ACATGCCCAA   300
 A  A  A    A  N  L  N   G  T  L    M  Q  Y    F  E  W  Y    M  P  N

TGACGGCCAA CATTGGAAGC GTTTGCAAAA CGACTCGGCA TATTTGGCTG AACACGGTAT   360
 D  G  Q    H  W  K  R   L  Q  N    D  S  A    Y  L  A  E    H  G  I

TACTGCCGTC TGGATTCCCC CGGCATATAA GGGAACGAGC CAAGCGGATG TGGGCTACGG   420
 T  A  V    W  I  P  P   A  Y  K    G  T  S    Q  A  D  V    G  Y  G

TGCTTACGAC CTTTATGATT TAGGGGAGTT TCATCAAAAA GGGACGGTTC GGACAAAGTA   480
 A  Y  D    L  Y  D  L   G  E  F    H  Q  K    G  T  V  R    T  K  Y

CGGCACAAAA GGAGAGCTGC AATCTGCGAT CAAAAGTCTT CATTCCCGCG ACATTAACGT   540
 G  T  K    G  E  L  Q   S  A  I    K  S  L    H  S  R  D    I  N  V

TTACGGGGAT GTGGTCATCA ACCACAAAGG CGGCGCTGAT GCGACCGAAG ATGTAACCGC   600
 Y  G  D    V  V  I  N   H  K  G    G  A  D    A  T  E  D    V  T  A

GGTTGAAGTC GATCCCGCTG ACCGCAACCG CGTAATTTCA GGAGAACACC TAATTAAAGC   660
 V  E  V    D  P  A  D   R  N  R    V  I  S    G  E  H  L    I  K  A
```

FIG._3A

```
CTGGACACAT TTTCATTTTC CGGGGCGCGG CAGCACATAC AGCGATTTTA AATGGCATTG    720
 W  T  H    F  H  F  P   G  R  G   S  T  Y    S  D  F  K    W  H  W

GTACCATTTT GACGGAACCG ATTGGGACGA GTCCCGAAAG CTGAACCCGCA TCTATAAGTT    780
 Y  H  F    D  G  T  D   I  G  T   V  P  K    L  N  R  I    Y  K  F

TCAAGGAAAG GCTTGGGATT GGGAAGTTTC CAATGAAAAC GGCAACTATG ATTATTTGAT    840
 Q  G  K    A  W  D  W   E  V  S   N  E  N    G  N  Y  D    Y  L  M

GTATGCCGAC ATCGATTATG ACCATCCTGA TGTCGCAGCA GAAATTAAGA GATGGGGCAC    900
 Y  A  D    I  D  Y  D   H  P  D   V  A  A    E  I  K  R    W  G  T

TTGGTATGCC AATGAACTGC AATTGGACGG TTTCCGTCTT GATGCTGTCA AACACATTAA    960
 W  Y  A    N  E  L  Q   L  D  G   F  R  L    D  A  V  K    H  I  K

ATTTTCTTTT TTGCGGGATT GGGTTAATCA TGTCAGGGAA AAAACGGGGA AGGAAATGTT   1020
 F  S  F    L  R  D  W   V  N  H   V  R  E    K  T  G  K    E  M  F

TACGGTAGCT GAATATTGGC AGAATGACTT GGGGCGCGCTG GAAAACTATT CAGTTCCATG   1080
 T  V  A    E  Y  W  Q   N  D  L   G  A  L    E  N  Y  L    Q  F  H

AAATTTAAT CATTCAGTGT TTGACGTGCC GCTTCATTAT GCTGAACGGT ACGGTCGTTT   1140
 N  F  N    H  S  V  F   D  V  P   L  H  Y    A  S  T

ACAGGGAGGC GGCTATGATA TGAGGAAATT TGATACACAG CCGGGGCAAT CCAAGCATCC   1200
 Q  G  G    G  Y  D  M   R  K  L   N  G  T    V  V  S  K    H  P

GTTGAAATCG GTTACATTTG TCGATAACCA TGATACACAG CCGGGGCAAT CGCTTGAGTC   1260
 L  K  S    V  T  F  V   D  N  H   D  T  Q    P  G  Q  S    L  E  S

GACTGTCCAA ACATGGTTTA AGCCGCTTGC TTACGCTTTT ATTCTCACAA GGGAATCTGG   1320
 T  V  Q    T  W  F  K   P  L  A   Y  A  F    I  L  T  R    E  S  G
```

FIG._3B

```
ATACCCTCAG GTTTTCTACG GGGATATGTA CGGGACCAAA GGAGACTCCC AGCGCGAAAT   1380
 Y  P  Q    V  F  Y  R    G  D  M  Y    G  T  K    G  D  S  Q    R  E  I

TCCTGCCTTG AAACACAAAA TTGAACCGAT CTTAAAAGCG AGAAAACAGT ATGCGTACGG   1440
 P  A  L    K  H  K  I    E  P  I    L  K  A    R  K  Q  Y    A  Y  G

AGCACAGCAT GATTATTTCG ACCACCATGA CATTGTCGGC TGGACAAGGG AAGGCGACAG   1500
 A  Q  H    D  Y  F  D    H  H  D    I  V  G    W  T  R  E    G  D  S

CTCGGGTTGCA AATTCAGGTT TGGCGGCATT AATAACAGAC GGACCCGGTG GGGCAAAGCG   1560
 S  V  A    N  S  G  L    A  A  L    I  T  D    G  P  G  G    A  K  R

AATGTATGTC GGCCCGGCAAA ACGCCGGTGA GACATGGCAT GAAACCGTTC   1620
 M  Y  V    G  R  Q  N    A  G  E    T  W  H    D  I  T  G    N  R  S

GGAGCCGGTT GTCATCAATT CGGAAGGCTG GGGAGAGTTT CACGTAAACG GCGGGTCGGT   1680
 E  P  V    V  I  N  S    E  G  W    G  E  F    H  V  N  G    G  S  V

TTCAATTTAT GTTCAAAGAT AGAAGAGCAG AGAGGACGGA TTTCCTGAAG GAAATCCGTT   1740
 S  I  Y    V  Q  R  *

TTTTTATTTT GCCCGTCTTA TAAATTTCTT TGATTACATT TTATAATTAA TTTTAACAAA   1800

GTGTCATCAG CCCTCAGGAA GGACTTGCTG ACAGTTTGAA TCGCATAGGT AAGGCGGGGA   1860

TGAAATGGCA ACGTTATCTG ATGTAGCAAA GAAAGCAAAT GTGTCGAAAA TGACGGTATC   1920

GCGGGTGATC AATCATCCTG AGACTGTGAC GGATGAATTG AAAAAGCT                1968
```

FIG._3C

```
ANLNGTLMQY FEWYMPNDGQ HWKRLQNDSA YLAEHGITAV WIPPAYKGTS QADVGYGAYD    60
LYDLGEFHQK GTVRTKYGTK GELQSAIKSL HSRDINVYGD VVINHKGAD  ATEDVTAVEV   120
DPADRNRVIS GEHLIKAWTH FHFPGRGSTY SDFKWHWYHF DGTDWDESRK LNRIYKFQGK   180
AWDWEVSNEN GNYDYLMYAD IDYDHPDVAA EIKRWGTWYA NELQLDGFRL DAVKHIKFSF   240
LRDWVNHVRE KTGKEMFTVA EYWQNDLGAL ENYLNKTNFN HSVFDVPLHY QFHAASTQGG   300
GYDMRKLLNG TVVSKHPLKS VIFVDNHDTQ PGQSLESTVQ TWFKPLAYAF ILTRESGYPQ   360
VFYGDMYGTK GDSQREIPAL KHKIEPILKA RKQYAYGAQH DYFDHHDIVG WTREGDSSVA   420
NSGLAALITD GPGGAKRMYV GRQNAGETWH DITGNRSEPV VINSEGWGEF HVNGGSVSIY   480
VQR
```

FIG._4

Am-Lich = B.llcheniformis   Am-Amylo = B.amyloliquefaciens   Am-Stero = B.stearothermophilus.

```
                   1                                                                              19
                                                                                                  1
                                                                                                  60
Am-Lich   ......MKQQ KRLYARLLTL LFALIFLLPH ......SAAA AANLNGTLMQ YFEWYMPNDG
Am-Amylo  MRGRGNMIQK RKRTVSFRLV LMCTLLFVSL ......PITK TSAVNGTLMQ YFEWYTPNDG
Am-Stearo ......VLTF HRIIRKGWMF LLAFLLTASL FCPTGRHAKA AAPFNGTMMQ YFEWYLPDDG 61                                                                             79
                                                                                                  120
Am-Lich   QHWKRLQNDS AYLAEHGITA VWIPPAYKGT SQADVGYGAY DLYDLGEFHQ KGTVRTKYGT
Am-Amylo  QHWKRLQNDA EHLSDIGITA VWIPPAYKGL SQSDNGYGPY DLYDLGEFQQ KGTVRTKYGT
Am-Stearo TLWTKVANEA NNLSSLGITA LSLPPAYKGT SRSDVGYGVY DLYDLGEFNQ KGTVRTKYGT 121                                                                            139
                                                                                                  180
Am-Lich   KGELQSAIKS LHSRDINVYG DVVINHKGGA DATEDVTAVE VDPADRNRVI SGEHLIKAWT
Am-Amylo  KSELQDAIGS LHSRNVQVYG DVVLNHKAGA DATEDVTAVE VNPANRNQET SEEYQIKAWT
Am-Stearo KAQYLQAIQA AHAAGMQVYA DVVFDHKGGA DGTEWVDAVE VNPSDRNQEI SGTYQIQAWT 181                                                                            197
                                                                                                  240
Am-Lich   HFHFPGRGST YSDFKWHWYH FDGTDWDESR KLNRIYKF.. QGKAWDWEVS NENGNYDYLM
Am-Amylo  DFRFPGRGNT YSDFKWHWYH FDGADWDESR KISRIFKFRG EGKAWDWEVS SENGNYDYLM
Am-Stearo KFDFPGRGNT YSSFKWRWYH FDGVDWDESR KLSRIYKFRG IGKAWDWEVD TENGNYDYLM 241                                                                            257
                                                                                                  300
Am-Lich   YADIDYDHPD VAAEIKRWGT WYANELQLDG FRLDAVKHIK FSFLRDWVNH VREKTGKEMF
Am-Amylo  YADVDYDHPD VVAETKKWGI WYANELSLDG FRIDAAKHIK FSFLRDWVQA VRQATGKEMF
Am-Stearo YADLDMDHPE VVTELKNWGK WYVNTTNIDG FRLDGLKHIK FSFFPDWLSY VRSQTGKPLF
```

FIG.—5A

Am-Lich   = B.llcheniformis   Am-Amylo = B.amyloliquefaciens   Am-Stero = B.stearothermophilus.

```
                 301                                                                              317
Am-Lich     TVAEYWQNDL GALENYLNKT NFNHSVFDVP LHYQFHAAST QGGGYDMRKL LNGTVVSKHP
Am-Amylo    TVAEYWQNNA GKLENYLNKT SFNQSVFDVP LHFNLQAASS QGGGYDMRRL LDGTVVSRHP
Am-Stearo   TVGEYWSYDI NKLHNYITKT NGTMSLFDAP LHNKFYTASK SGGAFDMRTL MTNTLMKDQP      360

361                                                                              377
Am-Lich     LKSVTFVDNH DTQPGQSLES TVQTWFKPLA YAFILTRESG YPQVFYGDMY GTKGDSQREI
Am-Amylo    EKAVTFVENH DTQPGQSLES TVQTWFKPLA YAFILTRESG YPQVFYGDMY GTKGTSPKEI
Am-Stearo   TLAVTFVDNH DTNPAKR.CS HGRPWFKPLA YAFILTRQEG YPCVFYGDYY GI...PQYNI       420

421                                                                              437
Am-Lich     PALKHKIEPI LKARKQYAYG AQHDYFDHHD IVGWTREGDS SVANSGLAAL ITDGPGGAKR
Am-Amylo    PSLKDNIEPI LKARKEYAYG PQHDYIDHPD VIGWTREGDS SAAKSGLAAL ITDGPGGSKR
Am-Stearo   PSLKSKIDPL LIARRDYAYG TQHDYLDHSD IIGWTREGVT EKPGSGLAAL ITDGAGRSKW       480

481                                                  483                          540
Am-Lich     MYVGRQNAGE TWHDITGNRS EPVVINSEGW GEFHVNGGSV SIYVQR.... ..........
Am-Amylo    MYAGLKNAGE TWYDITGNRS DTVKIGSDGW GEFHVNDGSV SIYVQK.... ..........
Am-Stearo   MYVGKQHAGK VFYDLTGNRS DTVTINSDGW GEFKVNGGSV SVWVPRKTTV STIARPITTR 541                    559
Am-Lich     .......... .........
Am-Amylo    .......... .........
Am-Stearo   PWTGEFVRWH EPRLVAWP*
```

FIG._5B

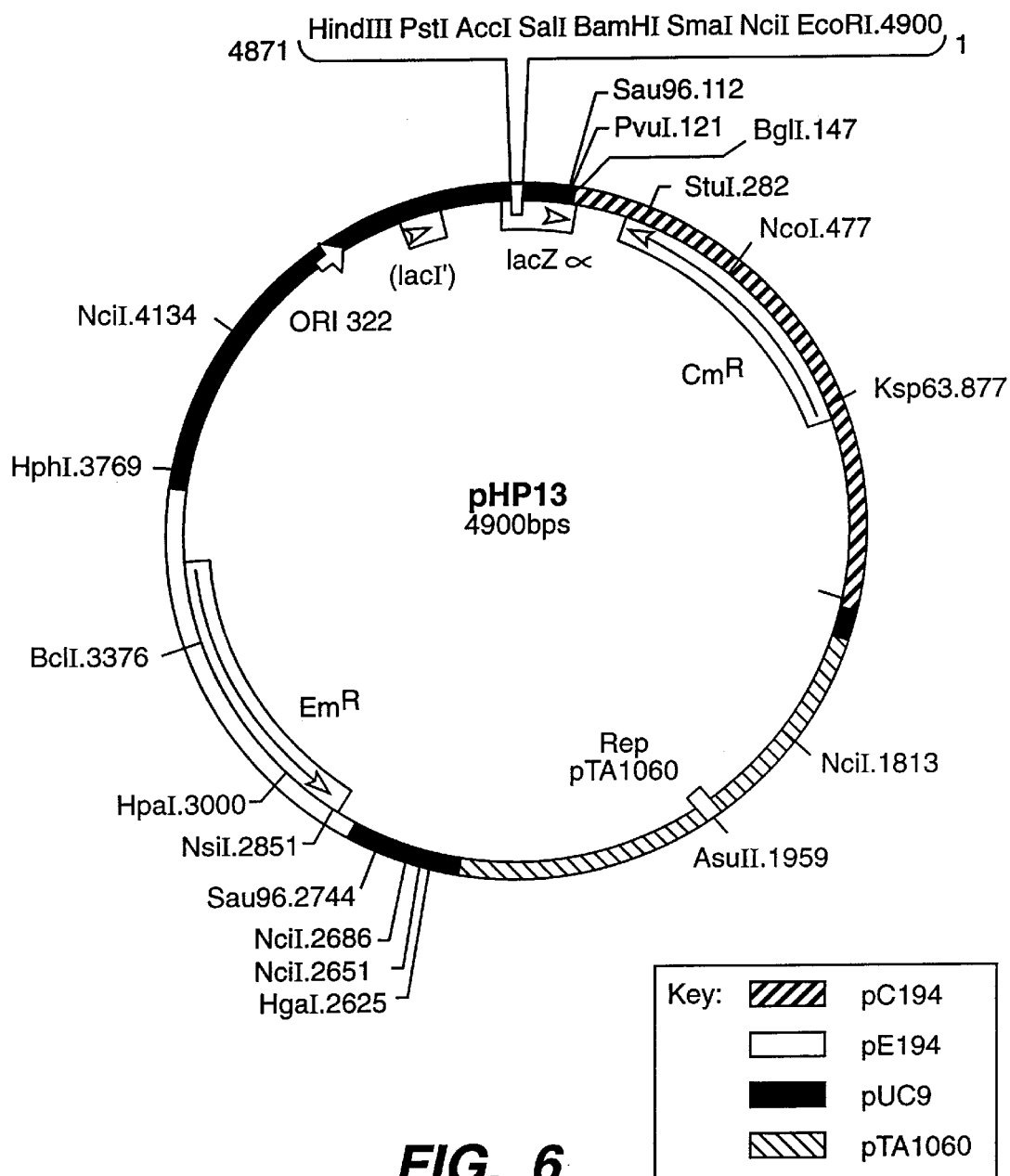
FIG._6

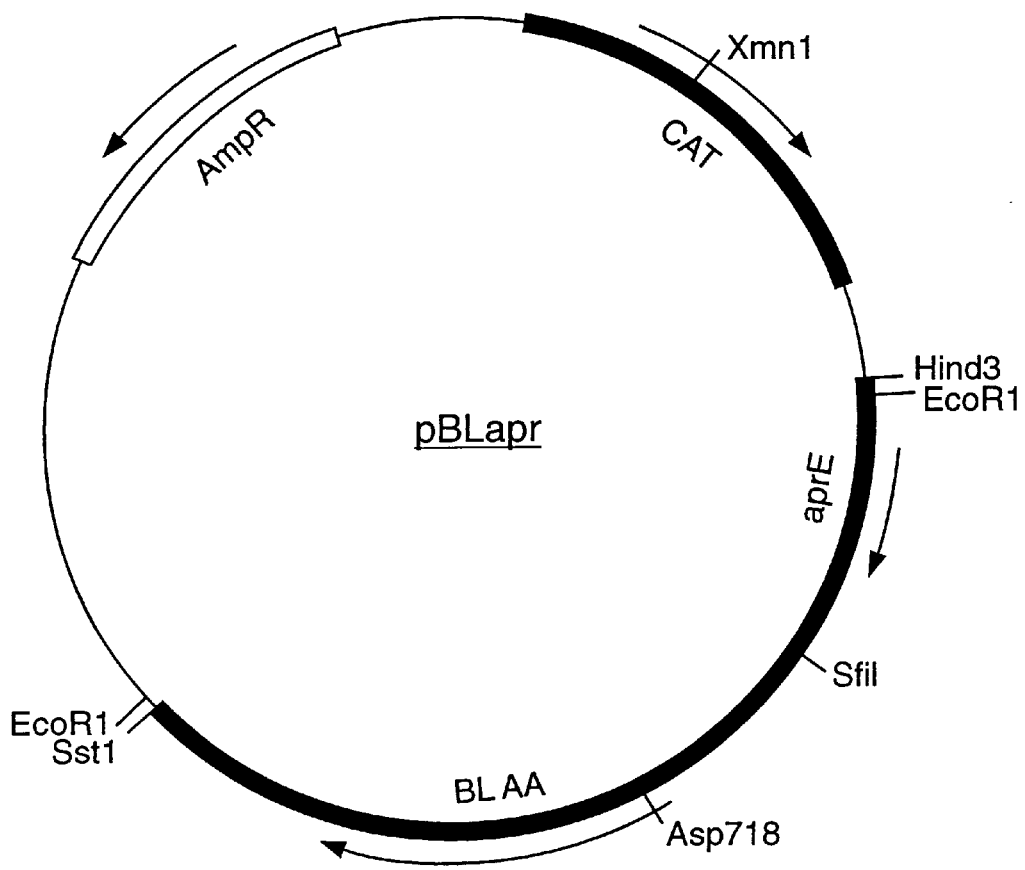
FIG._7

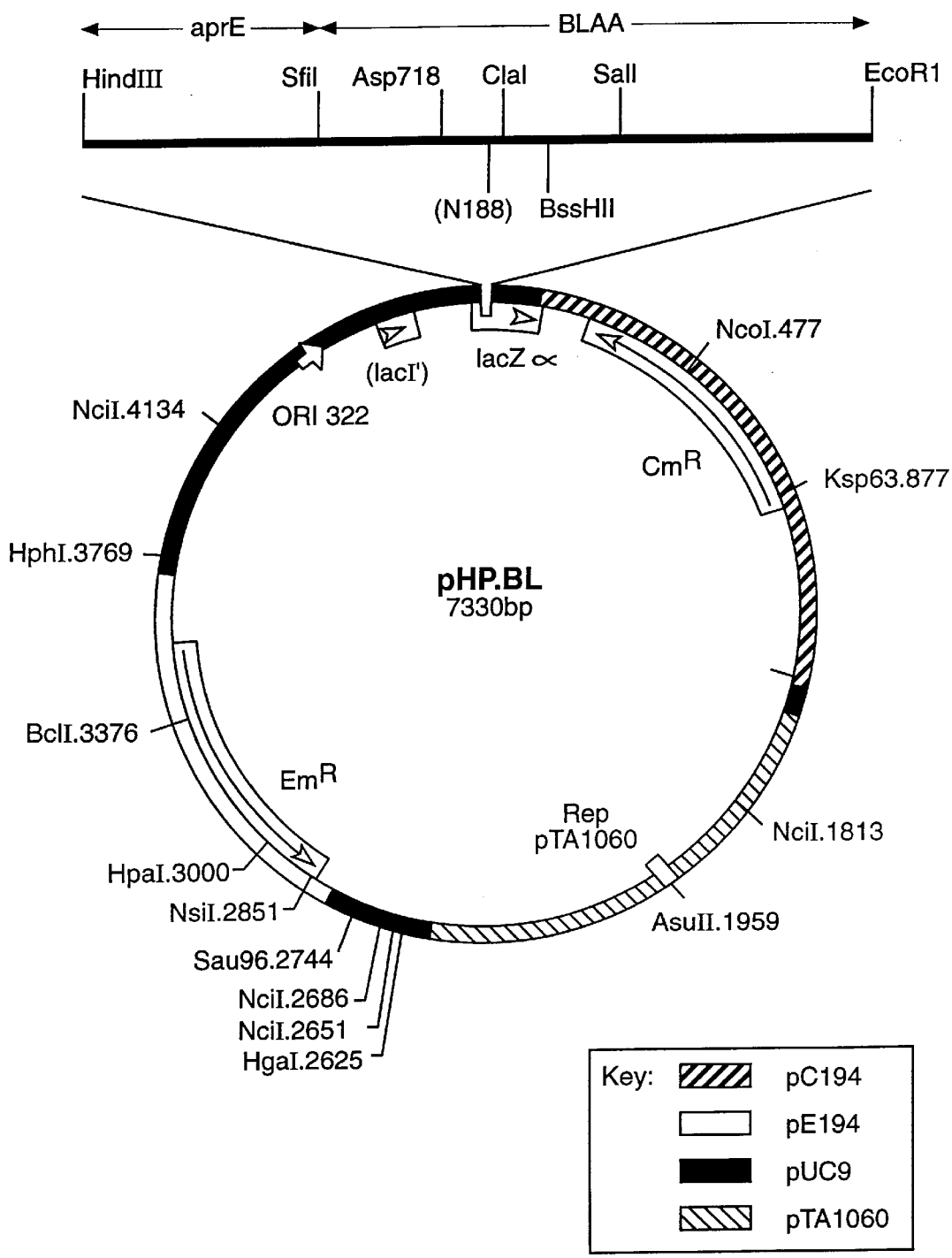
pHP.BL = pHP13 with the 2460bp HindIII-EcoRI insert from pBLapr
FIG._8

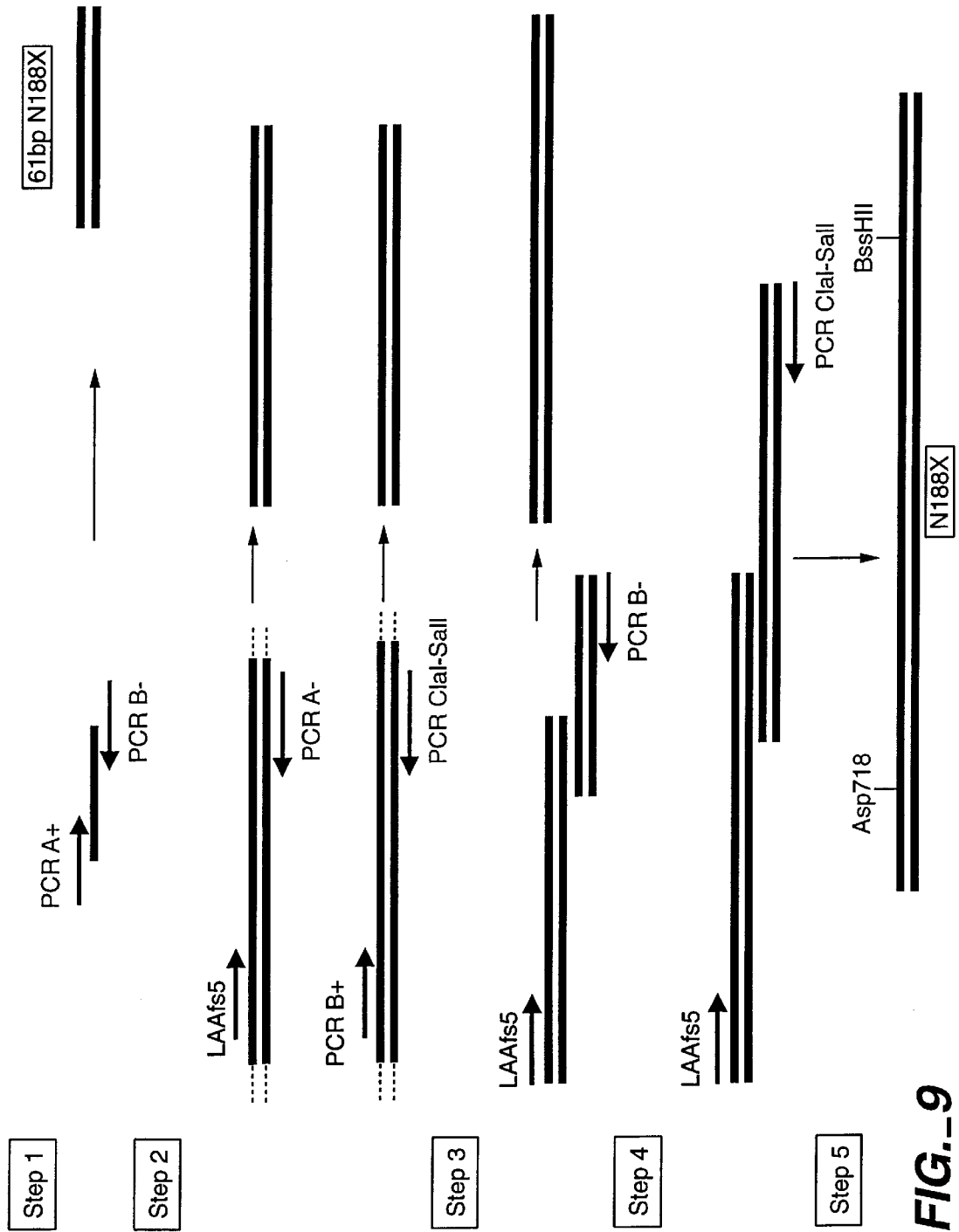
FIG._9

SIGNAL SEQUENCE-MATURE PROTEIN JUNCTIONS IN:

*B.licheniformis* alpha-amylase.

M K Q Q K R L T A R L L T L L F A L I F L L L P H S A A A A A N L ...
                                           (PstI)↓

*B.subtilis* alkaline protease aprE.

M R S K T L W I S L L F A L T L I F T M A F S N M S A Q A A G K S ...
                                    (PstI)↓

*B.licheniformis* alpha-amylase in pBLapr.

M R S K T L W I S L L F A L T L I F T M A F S N M S A Q A A N L ...

(PstI) → indicates the site of the restriction site in the gene

BOLD TYPE indicates the N-terminus of the secreted protein in *Bacillus*.

FIG._10

MUTANT α-AMYLASE

CROSS REFERENCE TO RELATED APPLICATIONS

This application is a continuation in part of U.S. Ser. No. 08/645,971 filed on May 14, 1996 U.S. Pat. No. 5,763,385.

FIELD OF THE INVENTION

The present invention is directed to α-amylases having altered performance characteristics. The present invention is also directed to novel mutant α-amylase enzymes having a mutation, wherein the resultant α-amylase exhibits improved specific activity and starch hydrolysis performance.

BACKGROUND OF THE INVENTION

α-Amylases (α-1,4-glucan4-glucanohydrolase, EC 3.2.1.1) hydrolyze internal α-1,4-glucosidic linkages in starch, largely at random, to produce smaller molecular weight malto-dextrins. α-Amylases are of considerable commercial value, being used in the initial stages (liquefaction) of starch processing; in alcohol production; as cleaning agents in detergent matrices; and in the textile industry for starch desizing. α-Amylases are produced by a wide variety of microorganisms including Bacillus and Aspergillus, with most commercial amylases being produced from bacterial sources such as *Bacillus licheniformis, Bacillus amyloliquefaciens, Bacillus subtilis,* or *Bacillus stearothermophilus.* In recent years, the preferred enzymes in commercial use have been those from *Bacillus licheniformis* because of their heat stability and performance, at least at neutral and mildly alkaline pH's.

In general, starch to fructose processing consists of four steps: liquefaction of granular starch, saccharification of the liquefied starch into dextrose, purification, and isomerization to fructose. The object of a starch liquefaction process is to convert a concentrated suspension of starch polymer granules into a solution of soluble shorter chain length dextrins of low viscosity. This step is essential for convenient handling with standard equipment and for efficient conversion to glucose or other sugars. To liquefy granular starch, it is necessary to gelatinize the granules by raising the temperature of the granular starch to over about 72° C. The heating process instantaneously disrupts the insoluble starch granules to produce a water soluble starch solution. The solubilized starch solution is then liquefied by α-amylase (EC 3.2.1.1.).

A common enzymatic liquefaction process involves adjusting the pH of a granular starch slurry to between 6.0 and 6.5, the pH optimum of α-amylase derived from *Bacillus licheniformis,* with the addition of calcium hydroxide, sodium hydroxide or sodium carbonate. The addition of calcium hydroxide has the advantage of also providing calcium ions which are known to stabilize the α-amylases against inactivation. Upon addition of α-amylases, the suspension is pumped through a steam jet to instantaneously raise the temperature to between 80–115° C. The starch is immediately gelatinized and, due to the presence of α-amylases, depolymerized through random hydrolysis of α(1–4) glycosidic bonds to a fluid mass which is easily pumped.

In a second variation to the liquefaction process, α-amylase is added to the starch suspension, the suspension is held at a temperature of 80–100° C. to partially hydrolyze the starch granules, and the partially hydrolyzed starch suspension is pumped through a jet at temperatures in excess of about 105° C. to thoroughly gelatinize any remaining granular structure. After cooling the gelatinized starch, a second addition of α-amylase can be made to further hydrolyze the starch.

A third variation of this process is called the dry milling process. In dry milling, whole grain is ground and combined with water. The germ is optionally removed by flotation separation or equivalent techniques. The resulting mixture, which contains starch, fiber, protein and other components of the grain, is liquefied using α-amylase. The general practice in the art is to undertake enzymatic liquefaction at a lower temperature when using the dry milling process. Generally, low temperature liquefaction is believed to be less efficient than high temperature liquefaction in converting starch to soluble dextrins.

Typically, after gelatinization the starch solution is held at an elevated temperature in the presence of α-amylase until a DE of 10–20 is achieved, usually a period of 1–3 hours. Dextrose equivalent (DE) is the industry standard for measuring the concentration of total reducing sugars, calculated as D-glucose on a dry weight basis. Unhydrolyzed granular starch has a DE of virtually zero, whereas the DE of D-glucose is defined as 100.

The maximum temperature at which the starch solution containing α-amylase can be held depends upon the microbial source from which the enzyme was obtained and the molecular structure of the α-amylase molecule. α-Amylases produced by wild type strains of *Bacillus subtilis* or *Bacillus amyloliquefaciens* are typically used at temperatures no greater than about 90° C. due to excessively rapid thermal inactivation above that temperature, whereas α-amylases produced by wild type strains of *Bacillus licheniformis* can be used at temperatures up to about 110° C. The presence of starch and calcium ion are known to stabilize α-amylases against inactivation. Nonetheless, α-amylases are used at pH values above 6 to protect against rapid inactivation. At low temperatures, α-amylase from *Bacillus licheniformis* is known to display hydrolyzing activity on starch substrate at pH values as low as 5. However, when the enzyme is used for starch hydrolysis at common jet temperatures, e.g., between 102° C. and 109° C., the pH must be maintained above at least pH 5.7 to avoid excessively rapid inactivation. The pH requirement unfortunately provides a narrow window of processing opportunity because pH values above 6.0 result in undesirable by-products, e.g., maltulose. Therefore, in reality, liquefaction pH is generally maintained between 5.9 and 6.0 to attain a satisfactory yield of hydrolyzed starch.

Another problem relating to pH of liquefaction is the need to raise the pH of the starch suspension from about 4, the pH of a corn starch suspension as it comes from the wet milling stage, to 5.9–6.0. This pH adjustment requires the costly addition of acid neutralizing chemicals and also requires additional ion-exchange refining of the final starch conversion product to remove the chemical. Moreover, the next process step after liquefaction, typically saccharification of the liquefied starch into glucose with glucoamylase, requires a pH of 4–4.5; therefore, the pH must be adjusted down from 5.0–6.0 to 4–4.5; requiring additional chemical addition and refining steps.

Subsequent to liquefaction, the processed starch is saccharified to glucose with glucoamylase. A problem with present processes occurs when residual starch is present in the saccharification mixture due to an incomplete liquefaction of the starch, e.g., inefficient amylose hydrolysis by amylase. Residual starch is highly resistant to glucoamylase hydrolysis. It represents a yield loss and interferes with downstream filtration of the syrups.

Additionally, many α-amylases are known to require the addition of calcium ion for stability. This further increases the cost of liquefaction.

In U.S. Pat. No. 5,322,778, liquefaction between pH 4.0 and 6.0 was achieved by adding an antioxidant such as bisulfite or a salt thereof, ascorbic acid or a salt thereof, erythorbic acid, or phenolic antioxidants such as butylated hydroxyanisole, butylated hydroxytoluene, or α-tocopherol to the liquefaction slurry. According to this patent, sodium bisulfite must be added in a concentration of greater than 5 mM.

In U.S. Pat. No. 5,180,669, liquefaction between a pH of 5.0 to 6.0 was achieved by the addition of carbonate ion in excess of the amount needed to buffer the solution to the ground starch slurry. Due to an increased pH effect which occurs with addition of carbonate ion, the slurry is generally neutralized by adding a source of hydrogen ion, for example, an inorganic acid such as hydrochloric acid or sulfuric acid.

In PCT Publication No. WO 94/02597, a mutant α-amylase having improved oxidative stability is described wherein one or more methionines are replaced by any amino acid except cysteine or methionine.

In PCT publication No. WO 94/18314, a mutant α-amylase having improved oxidative stability is described wherein one or more of the methionine, tryptophan, cysteine, histidine or tyrosine residues is replaced with a non-oxidizable amino acid.

In PCT Publication No. WO 91/00353, the performance characteristics and problems associated with liquefaction with wild type *Bacillus licheniformis* α-amylase are approached by genetically engineering the α-amylase to include the specific substitutions Ala-11 1-Thr, His-133-Tyr and/or Thr-149-Ile.

Studies using recombinant DNA techniques to explore which residues are important for the catalytic activity of amylases and/or to explore the effect of modifying certain amino acids within the active site of various amylases and glycosylases have been conducted by various researchers (Vihinen et al., *J. Biochem.*, Vol. 107, pp. 267–272 (1990); Holm et al., *Protein Engineering*, Vol. 3, pp. 181–191 (1990); Takase et al., *Biochemica et Biophysica Acta*, Vol. 1120, pp. 281–288 (1992); Matsui et al., *Febs Letters*, Vol. 310, pp. 216–218 (1992); Matsui et al., *Biochemistry*, Vol. 33, pp. 451–458 (1992); Sogaard et al., *J. Biol. Chem.*, Vol. 268, pp. 22480–22484 (1993); Sogaard et al., Carbohydrate Polymers, Vol. 21, pp. 137–146 (1993); Svensson, *Plant Mol. Biol.*, Vol. 25, pp.141–157 (1994); Svensson et al., *J. Biotech.*, Vol. 29, pp.1–37 (1993)). Researchers have also studied which residues are important for thermal stability (Suzuki et al., *J. Biol. Chem.* Vol. 264, pp.18933–18938 (1989); Watanabe et al., *Eur. J. Biochem.*, Vol. 226, pp. 277–283 (1994)); and one group has used such methods to introduce mutations at various histidine residues in a *Bacillus licheniformis* amylase, the rationale being that *Bacillus licheniformis* amylase which is known to be relatively thermostable when compared to other similar Bacillus amylases, has an excess of histidines and, therefore, it was suggested that replacing a histidine could affect the thermostability of the enzyme. This work resulted in the identification of stabilizing mutations at the histidine residue at the +133 position and the alanine residue at position +209 (Declerck et al., *J. Biol. Chem.*, Vol. 265, pp. 15481–15488 (1990); FR 2 665 178-A1; Joyet et al., *Bio/Technology*, Vol. 10, pp. 1579–1583 (1992)).

Despite the advances made in the prior art, a need exists for improved α-amylases which provide increased specific activity and/or liquefaction performance.

SUMMARY OF THE INVENTION

It is a further object of the present invention to provide an α-amylase having altered low pH stability for use in efficient low pH liquefaction.

It is yet a further object of the present invention to provide an α-amylase which allows efficient liquefaction of dry milled grain at high temperatures.

According to the present invention, an α-amylase is provided that comprises a mutation equivalent to G475R in *Bacillus licheniformis*. Preferably, the α-amylase further comprises the substitution of a methionine or tryptophan residue, particularly at a position corresponding to M15, W138, N188 and/or M197, or at a residue corresponding V128, H133, W138, V148, S187, A209 and/or A379 in *Bacillus licheniformis*. In a most preferred embodiment, an α-amylase is provided comprising substitutions at residues corresponding to M15T/H133Y/V148S/N188S/A209V/A379S/G475R in *Bacillus licheniformis*. The α-amylases of the invention are efficiently constructed using recombinant DNA technology.

DESCRIPTION OF THE DRAWINGS

FIG. 1 illustrates mutagenic oligonucleotides (SEQ ID NOS:4–22) useful during directed mutagenesis of Asn188 from *Bacillus licheniformis* α-amylase. In this and following figures illustrating oligonucleotide constructs, bold letters indicate base changes introduced by the oligonucleotide and underlining indicates restriction endonuclease sites introduced by the oligonucleotide.

FIG. 2 illustrates PCR primers (SEQ ID NOS:23–32) used for PCR processing of mutagenic oligonucleotide templates.

FIG. 3 illustrates the DNA sequence of the gene for α-amylase from *Bacillus licheniformis* (NCIB 8061) (SEQ ID NO:33) and deduced amino acid sequence of the translation product (SEQ ID NO:34) as described by Gray et al., J. Bacteriology, vol. 166, pp. 635–643 (1986).

FIG. 4 illustrates the amino acid sequence (SEQ ID NO:35) of the mature α-amylase enzyme from *Bacillus licheniformis*.

FIG. 5 illustrates an alignment of the primary structures of three Bacillus α-amylases. The *Bacillus licheniformis* α-amylase (Am-Lich) (SEQ ID NO:36) is described by Gray et al., *J. Bacteriology*, Vol. 166, pp. 635–643 (1986); the *Bacillus amyloliquefaciens* α-amylase (Am-Amylo) (SEQ ID NO:37) is described by Takkinen et al., *J. Biol. Chem.*, Vol. 258, pp. 1007–1013 (1983); and the *Bacillus stearothermophilus* α-amylase (Am-Stearo) (SEQ ID NO:38) is described by Ihara et al., *J. Biochem.*, Vol. 98, pp. 95–103 (1985).

FIG. 6 illustrates plasmid pHP13 wherein $Cm^R$ refers to chloramphenicol resistance, $Em^R$ refers to erythromycin resistance and Rep pTA1060 refers to the origin of replication from plasmid pTA1060.

FIG. 7 illustrates the pBLapr plasmid wherein BL AA refers to *Bacillus licheniformis* α-amylase gene; aprE refers to the promoter and signal peptide encoding region of the aprE gene; AmpR refers to the ampicillin resistant gene from pBR322; and CAT refers to the chloramphenicol resistance gene from pC194.

FIG. 8 illustrates the pHP.BL plasmid carrying the gene for *Bacillus licheniformis* α-amylase.

FIG. 9 illustrates a schematic of the PCR method used to produce the mutant oligonucleotides corresponding to α-amylase derived from *Bacillus licheniformis*.

FIG. 10 illustrates the signal sequence-mature protein junctions in α-amylase derived from *Bacillus licheniformis* (SEQ ID NO:39), *Bacillus subtilis* aprE (SEQ ID NO: 40) and *Bacillus licheniformis* in pBLapr (SEQ ID NO:41).

DETAILED DESCRIPTION

"α-Amylase" means an enzymatic activity which cleaves or hydrolyzes the α(1-4)glycosidic bond, e.g., that in starch, amylopectin or amylose polymers. α-Amylase may be derived from naturally occurring sources as well as recombinant α-amylases. Preferred α-amylases in the present invention are those derived from Bacillus, especially *Bacillus licheniformis, Bacillus amyloliquefaciens* or *Bacillus stearothermophilus*, as well as fungal α-amylases such as those derived from Aspergillus (i.e., *A. oryzae* and *A. niger*).

"Recombinant α-amylase" means an α-amylase in which the DNA sequence encoding the naturally occurring α-amylase is modified to produce a mutant DNA sequence which encodes the substitution, insertion or deletion of one or more amino acids in the α-amylase sequence compared to the naturally occurring α-amylase.

"Expression vector" means a DNA construct comprising a DNA sequence which is operably linked to a suitable control sequence capable of effecting the expression of said DNA in a suitable host. Such control sequences may include a promoter to effect transcription, an optional operator sequence to control such transcription, a sequence encoding suitable mRNA ribosome-binding sites, and sequences which control termination of transcription and translation. A preferred promoter is the *Bacillus subtilis* aprE promoter. The vector may be a plasmid, a phage particle, or simply a potential genomic insert. Once transformed into a suitable host, the vector may replicate and function independently of the host genome, or may, in some instances, integrate into the genome itself. In the present specification, plasmid and vector are sometimes used interchangeably as the plasmid is the most commonly used form of vector at present. However, the invention is intended to include such other forms of expression vectors which serve equivalent functions and which are, or become, known in the art.

"Host strain" or "host cell" means a suitable host for an expression vector comprising DNA encoding the α-amylase according to the present invention. Host cells useful in the present invention are generally procaryotic or eucaryotic hosts, including any transformable microorganism in which the expression of α-amylase according to the present invention can be achieved. Specifically, host strains of the same species or genus from which the α-amylase is derived are suitable, such as a Bacillus strain. Preferably, an α-amylase negative Bacillus strain (genes deleted) and/or an α-amylase and protease deleted Bacillus strain (ΔamyE, Δapr, npr) is used. Host cells are transformed or transfected with vectors constructed using common techniques. Such transformed host cells are capable of either replicating vectors encoding the α-amylase and its variants (mutants) or expressing the desired α-amylase.

"Liquefaction" or "liquefy" means a process by which starch is converted to shorter chain and less viscous dextrins. Generally, this process involves gelatinization of starch simultaneously with or followed by the addition of α-amylase.

According to the present invention, an α-amylase is provided that has a mutation corresponding to G475R in α-amylase from *Bacillus licheniformis*. Preferably, the α-amylase is the expression product of a mutated DNA sequence encoding an α-amylase, the mutated DNA sequence being derived from a precursor α-amylase by the substitution of G475R in *Bacillus licheniformis*. Also provided is a nucleic acid molecule (DNA) which encodes an amino acid sequence comprising at least a part of the α-amylase provided by the present invention, expression systems incorporating such DNA including vectors and phages, host cells transformed with such DNA, and anti-sense strands of DNA corresponding to the DNA molecule which encodes the amino acid sequence. Similarly, the present invention includes a method for producing an α-amylase by expressing the DNA incorporated on an expression system which has been transformed into a host cell. The α-amylase of the invention may be used in liquefaction of starch, as an ingredient in detergents, in food processing, in textile processing, or in any other application in which improved α-amylase activity is useful.

The α-amylases according to the present invention comprise an amino acid sequence which is derived from the amino acid sequence of a precursor α-amylase. The precursor α-amylases include naturally occurring α-amylases and recombinant α-amylases. The amino acid sequence of the α-amylase mutant is derived from the precursor α-amylase amino acid sequence by the substitution of one or more amino acids of the precursor amino acid sequence. Such modification is generally of the DNA which encodes the precursor α-amylase rather than manipulation of the precursor α-amylase enzyme per se. Suitable methods for such manipulation of the precursor DNA sequence include methods disclosed herein and in commonly owned U.S. Pat. Nos. 4,760,025 and 5,185,258, incorporated herein by reference.

The α-amylases according to the present invention are derived from a precursor amylase. The precursor α-amylase is produced by any source capable of producing α-amylase. Suitable sources of α-amylases are prokaryotic or eukaryotic organisms, including fungi, bacteria, plants or animals. Preferably, the precursor α-amylase is produced by a Bacillus; more preferably, by *Bacillus licheniformis, Bacillus amyloliquefaciens* or *Bacillus stearothermophilus*, most preferably, the precursor α-amylase is derived from *Bacillus licheniformis*.

Homologies have been found between almost all endo-amylases sequenced to date, ranging from plants, mammals, and bacteria (Nakajima et al., *Appl. Microbiol. Biotechnol.,* Vol. 23, pp. 355–360 (1986); Rogers, *Biochem. Biophys. Res. Commun.,* Vol. 128, pp. 470–476 (1985); Janecek, *Eur. J. Biochem.,* Vol. 224, pp. 519–524 (1994)). There are four areas of particularly high homology in certain Bacillus amylases, as shown in FIG. 5 (SEQ ID NOS:36–38), wherein the underlined sections designate the areas of high homology. Sequence alignments have also been used to map the relationship between Bacillus endo-amylases (Feng et al., *J. Molec. Evol.,* Vol. 35, pp. 351–360 (1987)). The relative sequence homology between *Bacillus stearothermophilus* and *Bacillus licheniformis* amylase is about 66% and that between *Bacillus licheniformis* and *Bacillus amyloliquefaciens* amylases is about 81%, as determined by Holm et al., *Protein Engineering,* Vol. 3, No. 3, pp. 181–191 (1990). While sequence homology is important, it is generally recognized that structural homology is also important in comparing amylases or other enzymes. For example, structural homology between fungal amylases and bacterial amylase has been suggested and, therefore, fungal amylases are encompassed within the present invention.

Specific residues referred to herein such as G475 refer to an amino acid position number (i.e., +475) which references the number assigned to the mature *Bacillus licheniformis* α-amylase sequence (SEQ ID NO:35) illustrated in FIG. 4. The invention, however, is not limited to the mutation of the particular mature α-amylase of *Bacillus licheniformis* but extends to precursor α-amylases containing amino acid residues at positions which are equivalent to the particular identified residue in *Bacillus licheniformis* α-amylase. A residue of a precursor α-amylase is equivalent to or corresponds to a residue of *Bacillus licheniformis* α-amylase if it is either homologous (i.e., corresponds in position for either the primary or tertiary structure) or analogous to a specific residue or portion of that residue in *Bacillus licheniformis* α-amylase (i.e., having the same or similar functional capacity to combine, react, or interact chemically or structurally).

In order to establish homology to primary structure, the amino acid sequence of a precursor α-amylase is directly compared to the *Bacillus licheniformis* α-amylase primary sequence and particularly to a set of residues known to be invariant to all α-amylases for which sequences are known (see e.g., FIG. 7). It is possible also to determine equivalent residues by tertiary structure analysis of the crystal structures reported for porcine pancreatic α-amylase (Buisson et al., *EMBO Journal,* Vol. 6, pp. 3909–3916 (1987); Qian et al., *Biochemistry,* Vol. 33, pp. 6284–6294 (1994); Larson et al., *J. Mol. Biol.,* Vol. 235, pp. 1560–1584 (1994)); Taka-amylase A from *Aspergillus oryzae* (Matsuura et al., *J. Biochem.* (Tokyo), Vol. 95, pp. 697–702 (1984)); and an acid α-amylase from *A. niger* (Boel et al.. *Biochemistry,* Vol. 29, pp. 6244–6249 (1990)), with the former two structures being similar, and for barley α-amylase (Vallee et al., pp. 368–371 (1994); Kadziola, *J. Mol. Biol.,* Vol. 239, pp. 104–121 (1994)). Although there have been some preliminary studies published (Suzuki et al, *J. Biochem.,* Vol. 108, pp. 379–381 (1990); Lee et al., *Arch. Biochem. Biophys,* Vol. 291, pp. 255–257 (1991); Chang et al., *J. Mol. Biol.,* Vol. 229, pp. 235–238 (1993); Mizuno et al., *J. Mol. Biol.,* Vol. 234, pp. 1282–1283 (1993)), there is only a published structure for *Bacillus licheniformis* α-amylase (Machius et al., *J. Mol. Biol.,* Vol. 246, pp. 545–549 (1995)). However, several researchers have predicted common super-secondary structures between glucanases (MacGregor et al., *Biochem. J.,* Vol. 259, pp. 145–152 (1989)) and within α-amylases and other starch-metabolising enzymes (Jaspersen, *J. Prot Chem.,* Vol. 12, pp. 791–805 (1993); MacGregor, *Starke,* Vol. 45, pp. 232–237 (1993)); and sequence similarities between enzymes with similar super-secondary structures to α-amylases (Janecek, *FEBS Letters,* Vol. 316, pp. 23–26 (1993); Janecek et al., *J. Prot Chem.,* Vol. 12, pp. 509–514 (1993)). A structure for the *Bacillus stearothermophilus* enzyme has been modeled on that of Taka-amylase A (Holm et al., *Protein Engineering,* Vol. 3, pp. 181–191 (1990)). The four highly conserved regions shown in FIG. 7 contain many residues thought to be part of the active-site (Matsuura et al., *J. Biochem.* (Tokyo), Vol. 95, pp. 697–702 (1984); Buisson et al., *EMBO Journal,* Vol. 6, pp. 3909–3916 (1987); Vihinen et al., *J. Biochem.,* Vol. 107, pp. 267–272 (1990)) including His +105; Arg +229; Asp +231; His +235; Glu +261 and Asp +328 under the *Bacillus licheniformis* numbering system.

The α-amylases according to the present invention exhibit improved specific activity and liquefaction performance providing desirable and unexpected results which are useful in the various applications for which α-amylases are commonly used. The α-amylase of the present invention is especially useful in starch processing and particularly in starch liquefaction. Conditions present during commercially desirable liquefaction processes characteristically include low pH, high temperature and potential oxidation conditions requiring α-amylases exhibiting improved low pH performance, improved thermal stability and improved oxidative stability. Accordingly, α-amylases according to the present invention which are particularly useful in liquefaction exhibit improved performance at a pH of less than about 6, preferably less than about 5.5, and most preferably between about 5.0 and 5.5. Additionally, α-amylases according to the present invention which exhibit increased thermal stability at temperatures of between about 80–120° C., and preferably between about 100–110° C., and increased stability in the presence of oxidants will be particularly useful. Preferably, the α-amylase according to the present invention which is used in liquefaction, in addition to substitution of a residue corresponding to G475, further comprises a deletion or substitution at one or more residues corresponding to M15, V128, H133, W138, V148, S187, M197, A209 and/or A379 in *Bacillus licheniformis*. Most preferably, the amylase comprises a substitution corresponding to M15T/H133Y/V148S/N188SA209V/A379S/G475R in *Bacillus licheniformis*. In any event, because it is contemplated that many mutations provide incremental advantages, the combination of such a mutation with the mutants of the invention should provide additive benefits. Thus, for example, because a mutation corresponding to M197T has been established as providing exceptional oxidation stability, the addition of a M197T modification to a mutant α-amylase of the invention should provide a similar boost in oxidative stability.

Additional components known by those skilled in the art to be useful in liquefaction, including, for example, antioxidants, calcium, ions, salts or other enzymes such as endoglycosidases, cellulases, proteases, lipases or other amylase enzymes may be added depending on the intended reaction conditions. For example, combinations of the α-amylase according to the present invention with α-amylases from other sources may provide unique action profiles which find particular use under specific liquefaction conditions. In particular, it is contemplated that the combination of the α-amylase according to the present invention with α-amylase derived from *Bacillus stearothermophilus* will provide enhanced liquefaction at pH values below 5.5 due to complementary action patterns. A preferred embodiment where the process involves the liquefaction of dry milled starch for ethanol production comprises α-amylase derived from *Bacillus stearothermophilus* and α-amylase according to the present invention.

During liquefaction, starch, specifically granular starch slurries from either a wet or dry milled process, is treated with an α-amylase of the present invention according to known liquefaction techniques. Generally, in the first step of the starch degradation process, the starch slurry is gelatinized by heating at a relatively high temperature (between about 80° C. and about 110° C). After the starch slurry is gelatinized, it is liquefied using an α-amylase.

In another embodiment of the present invention there are provided detergent compositions in either liquid, gel or granular form, which comprise the α-amylase according to the present invention. Such detergent compositions will particularly benefit from the addition of an α-amylase according to the present invention which has increased thermal stability to improve shelf-life or increased oxidative stability such that the α-amylase has improved resistance to bleach or peracid compounds commonly present in detergents. Thus, α-amylase according to the present invention may be advantageously formulated into known powdered, liquid or gel detergents having a pH of between about 6.5 and about 12.0. A preferred embodiment of the present invention further comprises the deletion or substitution of a methionine residue or a tryptophan residue, for example M15, M197 or W138 as described in commonly assigned U.S. patent application Ser. Nos. 08/289,351 and 08/409, 771, the disclosures of which are incorporated by reference; substitution at M133Y as described in PCT Publication No. WO 91/00353; or substitution at A209 as described in DeClerck, et al., *J. Biol. Chem.*, Vol. 265, pp. 15481–15488 (1990). Also preferably, an α-amylase according to the present invention used in detergent compositions. Detergent compositions comprising the α-amylase according to the present invention may further include other enzymes such as endoglycosidases, cellulases, proteases, lipases or other amylase enzymes, particularly α-amylase derived from *Bacillis stearothermophilus,* as well as additional ingredients as generally known in the art.

Embodiments of the present invention which comprise a combination of the α-amylase according to the present invention with protease enzymes preferably include oxidatively stable proteases such as those described in U.S. Pat. No. Re. 34,606, incorporated herein by reference, as well as commercially available enzymes such as DURAZYM (Novo Nordisk), MAXAPEM (Gist-brocades) and PURAFECT® OxP (Genencor International, Inc.). Methods for making such protease mutants (oxidatively stable proteases), and particularly such mutants having a substitution for the methionine at a position equivalent to M222 in *Bacillus amyloliquefaciens,* are described in U.S. Pat. No. Re. 34,606.

An additional embodiment of the present invention comprises DNA encoding an α-amylase according to the present invention and expression vectors comprising such DNA. The DNA sequences may be expressed by operably linking them to an expression control sequence in an appropriate expression vector and employing that expression vector to transform an appropriate host according to well known techniques. A wide variety of host/expression vector combinations may be employed in expressing the DNA sequences of this invention. Useful expression vectors, for example, include segments of chromosomal, non-chromosomal and synthetic DNA sequences, such as the various known plasmids and phages useful for this purpose.

In addition, any of a wide variety of expression control sequences are generally used in these vectors. For example, Applicants have discovered that a preferred expression control sequence for Bacillus transformants is the aprE signal peptide derived from *Bacillus subtilis.*

A wide variety of host cells are also useful in expressing the DNA sequences of this invention. These hosts may include well known eukaryotic and prokaryotic hosts, such as strains of *E. coli,* Pseudomonas, Bacillus, Streptomyces, various fungi, yeast and animal cells. Preferably, the host expresses the α-amylase of the present invention extracellularly to facilitate purification and downstream processing. Expression and purification of the mutant α-amylase of the invention may be effected through art-recognized means for carrying out such processes.

The improved α-amylases according to the present invention provide several important advantages when compared to wild type Bacillus α-amylases. For example, one advantage is the increased activity found at low pH and high temperatures typical of common starch liquefaction methods. Another advantage is the increased high pH and oxidative stability which facilitates their use in detergents. Another advantage is that a more complete hydrolysis of starch molecules is achieved which reduces residual starch in the processing stream. Yet another advantage is their improved stability in the absence of calcium ion. Yet another advantage is that the addition of equal protein doses of α-amylase according to the invention provide superior performance when compared to wild type *Bacillus licheniformis* α-amylase due to improvements in both specific activity and stability under stressed conditions. In other words, because of the generally increased stability of the amylases according to the present invention, the increased specific activity on starch of the inventive amylases translates to even greater potential performance benefits of this variant. Under conditions where the wild type enzyme is being inactivated, not only does more of the inventive amylase survive because of its increased stability, but also that which does survive expresses proportionally more activity because of its increased specific activity.

The following is presented by way of example and is not to be construed as a limitation to the scope of the claims. Abbreviations used herein, particularly three letter or one letter notations for amino acids are described in Dale, J. W., *Molecular Genetics of Bacteria,* John Wiley & Sons, (1989) Appendix B.

EXAMPLES

EXAMPLE 1

Construction Of Plasmid pHP.BL

The α-amylase gene (SEQ ID NO:33) shown in FIG. 3 was cloned from *Bacillus licheniformis* NCIB8061 (Gray et al., *J. Bacteriology,* Vol. 166, pp. 635–643 (1986)). The 1.72 kb PstI-SstI fragment, encoding the last three residues of the signal sequence, the entire mature protein and the terminator region, was subcloned into M13mp18. A synthetic terminator was added between the BclI and SstI sites using a synthetic oligonucleotide cassette of the form:

```
BcII                                                                    SstI
5'-GATCAAAACATAAAAAACCGGCCTTGGCCCCGCCGGTTTTTTATTATTTTTGAGCT-3'  (SEQ ID NO:1)
3'     TTTTGTATTTTTTGGCCGGAACCGGGGCGGCCAAAAAATAATAAAAAC    5'  (SEQ ID NO:2)
``` designed to contain the *Bacillus amyloliquefaciens* subtilisin transcriptional terminator (Wells et al., *Nucleic Acid Research,* Vol. 11, pp. 7911–7925 (1983)).

The pBLapr plasmid was constructed carrying the gene for the *Bacillus licheniformis* α-amylase. As illustrated in FIG. 7, pBLapr comprises a 6.1 kb plasmid including the ampicillin resistance gene from pBR322 and the chloramphenicol resistance gene from pC194, the aprE promoter and the gene encoding for the *Bacillus licheniformis* α-amylase ("BL AA"). The aprE promoter was constructed from a 660 bp HindIII-PstI fragment encoding for the promoter and signal sequence of the *Bacillus subtilis* alkaline protease. The PstI site was removed, and an SfiI site added close to the aprE/BL AA junction. The BL AA gene comprises the 1720 bp PstI-SstI fragment described above. In the work described herein, pBLapr was constructed with an SfiI site adjacent to the 5' end of the start of the coding sequence for the mature amylase gene. Specifically, the 5' end of the pBLapr construction was subcloned on an EcoRI-SstII fragment from pBLapr into M13BM20 (Boehringer Mannheim) to obtain a coding-strand template for the mutagenic oligonucleotide below:

5'-CCC ATT AAG ATT GGC CGC CTG GGC CGA CAT GTT GCT GG-3' (SEQ ID NO:3)

This primer introduced an SfiI site (indicated by underlining) which allowed correct forms to be screened for by the presence of this unique restriction site. Subcloning the EcoRI-SstII fragment back into the pBLapr vector gave a version of the plasmid containing an SfiI site.

Plasmid pHP13 (Haima et al., *Mol. Gen. Genet,* Vol. 209. pp. 335–342 (1987)) (FIG. 6) was digested with restriction enzymes EcoRI and HindIII and the resulting vector purified on a polyacrymide gel and then eluted. Plasmid pBLapr was digested with HindIII, Asp718 and in a separate incubation with Asp718, EcoRI and gel purified. Two bands, HindIII-Asp718 (1203 bp) and Asp718-EcoRI (1253 bp) were gel purified, eluted from the gel and ligated into the vector by a sway ligation, to give plasmid pHP.BL, the plasmid used in expression of the α-amylase (FIG. 8).

EXAMPLE 2

Construction Of Plasmids Encoding Mutant α-Amylases

This example will describe a series of mutagenic primers encoding for substitutions of Asn188 ("N188") with each of the naturally occurring amino acids were synthesized and are shown in FIG. 1 (SEQ ID NOS:4–22). However, the techniques described herein can easily be adapted to make further mutations in an expressed α-amylase. The α-amylase gene mutations encoding for these changes were made by PCR, according to the procedure summarized in FIG. 9, using the PCR primers shown in FIG. 2 (SEQ ID NOS:23–32).

Step (1): The mutagenic primers were used as templates for the PCR primers PCR A+ and PCR B– resulting in a lengthened (61 bp) double stranded DNA. Each contained a different amino acid replacement at position 188, and all except N188M contained a different restriction site. Initially the PCR primers were annealed at 35° C. for five minutes followed by a one minute DNA extension with taq polymerase at 75° C. The double stranded DNA was then melted at 95° C. for one minute, followed by the annealing and extension steps. Melting, annealing and extension continued for a total of 30 cycles.

Step (2): DNA upstream and downstream of position 188 were made in separate PCR reactions. The template was pBLapr, and the PCR primers were LAAfs5 (SEQ ID NO:27) and PCR A– (SEQ ID NO:24) for upstream; and PCR B+ (SEQ ID NO:25) and PCR Cla-SaII (SEQ ID NO:28) for downstream DNA. The DNA was melted at 95° C. for one minute, annealed at 45° C. for three minutes and elongated at 68° C. for 3 minutes. The upstream portion is 290 bp and downstream is 498 bp. This procedure was repeated for 18 cycles using pfu polymerase. The same PCR procedure was used in steps (3) and (4).

Step (3): The upstream portion of DNA described in step (2) was attached to the double stranded mutagenic primers described in step (1). Primers LAAfs5 (SEQ ID NO:27) and PCR B– (SEQ ID NO:26) were used. As the result of primer design there is a 24 bp overlap between these templates allowing for the attachment of the two pieces of DNA.

Step (4): The downstream portions of DNA described in Step (2) and the product of Step (3) were attached to give the final product A 24 bp overlap between the two PCR products allows for the attachment. Primers used were LAAfs5 (SEQ ID NO:27) and PCR ClaI-SaII (SEQ ID NO:28).

Step (5): Unique restriction sites, Asp718 and BssHII, are located upstream and downstream, respectively, of the 188 site. The final PCR product is digested with Asp718 and BssHII, the 333 bp fragment isolated by polyacrylamide gel electrophoresis and subcloned into the pHP.BL vector to obtain pHP.N188X.

Mutations were confirmed by dideoxy sequencing (Sanger et al., *Proc. Natl. Acad. Sci. U.S.A.,* Vol. 74, pp. 5463–5467 (1977)).

With reference to the DNA sequence (SEQ ID NO:33) and numbering system used in FIG. 3, the codon encoding for the +188 amino acid position is at base pairs 812–814. PCR primers A+ and A– correspond to base pairs 784–807. PCR primers B+ and B– correspond to base pairs 821–844. The 5' end of PCR primer LAAfs5 corresponds to base pair 518. The 5' end of PCR primer PCR ClaI-SaII corresponds to base pair 1317. The Asp718 site corresponds to base pair 724. The BssHII site corresponds to base pair 1053.

EXAMPLE 3

Construction Of Plasmid Encoding Mutations According To The Invention

A pBLapr plasmid having threonine substituted for methionine at amino acid 15 was constructed according to U.S. patent application Ser. No. 08/194,664 (PCT Publication No. WO 94/18314). This plasmid (pBLaprM15T) was digested with SfiI and Asp718, and the 477 base pair fragment subcloned into pHP.BL to create pHP.M15T. In a manner analogous to that described above, Example 1, pHP.M15T was digested with Asp718 and BssHII, gel purified and eluted from the gel. The 333 base pair fragment comprising Asp718 to BssHII and the fragment from pHP.N188S were then subcloned into pHP.M15T to give plasmid pHP.M15T/N188S. In an analogous manner, starting with plasmids pBL aprM15L and pHP.N188Y, the plasmid pHP. M15L/N188Y was constructed. Construction of plasmids encoding mutations of M15T/H133Y/N188S/A209V, M15T/H133Y/V148S/N188S/A209V/A379S, and M15T/H133Y/V148S/N188S/A209V/A379S/G475R in *Bacillus licheniformis* were made using similar principles.

EXAMPLE 4

Transformation Of Plasmids Into *Bacillus subtilis*, Expression And Purification of Mutant α-Amylase α-Amylase is expressed in *Bacillus subtilis* after transformation with the plasmids described in Examples 1–3. pHP13 is a plasmid able to replicate in *E. coli* and in *Bacillus subtilis*. Plasmids containing different variants are constructed using an appropriate *E. coli* strain, e.g., *E. coli* MM294. The plasmids isolated and then transformed into *Bacillus subtilis* as described in Anagnostopoulos et al., *J. Bacter.,* Vol. 81, pp. 741–746 (1961). The Bacillus strain is deleted for two proteases (Δapr, Δnpr) (see e.g., Ferrari et al., U.S. Pat. No. 5,264,366) and for amylase (ΔamyE) (see e.g., Stahl et al., *J. Bacter.,* Vol. 158, pp. 411–418 (1984)). After transformation, the sacU(Hy) mutation (Henner et al., *J. Bacter.,* Vol., 170, pp. 296–300 (1988)) is introduced by PBS-1 mediated transduction (Hoch,, *J. Bacter.,* Vol. 154, pp. 1513–1515 (1983)).

Secreted amylases are routinely recovered from *Bacillus subtilis* cultures constructed as provided above as follows: Secreted amylases are routinely recovered from *Bacillus*

*subtilis* cultures constructed as provided above as follows: Culture supernatants are heated to 75° C. for 15 mins, filtered through a 0.45 uM filter, and then dialysed against 20 mM ammonium acetate, pH6.0, 1 mM calcium chloride. This level of purification is sufficient for inactivation rate measurements and for liquefaction testing. For specific activity determinations the amylase is purified further by ion-exchange chromatography: The amylase is applied to a cation-exchange resin column (HS-M, Perseptive Biosystems) at pH5.0 in a loading buffer of 50 mM sodium acetate, pH5.0, 5 mM calcium chloride. The bound amylase is then eluted by a sodium chloride gradient, from 0 to 400 mM. Active amylase fractions are then pooled and dialysed against 20 mM ammonium acetate, pH6.0, 1 mM calcium chloride.

EXAMPLE 5

Specific Activity of Mutant α-Amylases on Soluble Substrate

Soluble Substrate Assay: A rate assay was developed based on an end-point assay kit supplied by Megazyme (Aust.) Pty. Ltd. A vial of substrate (p-nitrophenyl maltoheptaoside, BPNPG7) was dissolved in 10 ml of sterile water followed by a 1:4 dilution in assay buffer (50 mM maleate buffer, pH 6.7, 5 mM calcium chloride, 0.002% Tween20). Assays were performed by adding 10 µl of amylase to 790 µl of the substrate in a cuvette at 25° C. Rates of hydrolysis were measured as the rate of change of absorbance at 410 nm, after a delay of 75 seconds. The assay was linear up to rates of 0.2 absorption units/min. Protein concentration was determined by UV-absorbance spectroscopy, using a molar extinction coefficient for amylase of 143255 $M^{-1}$ at 278 nm.

α-Amylase protein concentration was measured using the standard Bio-Rad Assay (Bio-Rad Laboratories) based on the method of Bradford, *Anal. Biochem.*, Vol. 72, p. 248 (1976) using bovine serum albumin standards.

Starch Hydrolysis Assay: α-Amylase activity on starch was determined through an assay which depends on the ability of starch to form a blue colored complex with iodine and the disappearance of this color when starch is hydrolyzed to shorter dextrin molecules. The α-amylase activity was defined in terms of the digestion time required to produce a color change denoting a definite state of dextrination of the starch.

Reagents used were as follows:

Phosphate buffer—Potassium dihydrogen phosphate (340 g) and sodium hydroxide (25.3 g) were dissolved in water and diluted to ~two liters. The buffer was cooled to room temperature and the pH was adjusted to 6.2±0.1. The buffer was diluted to two liters in a volumetric flask.

Starch substrate—Ten grams (dry substance) of soluble lintner starch were suspended in 50 ml of water and washed into ~300 ml of boiling water. The suspension was again brought to boiling and was boiled for five minutes with constant stirring. The starch solution was cooled with constant stirring to room temperature and 125 ml of phosphate buffer was added. The solution was diluted to 500 ml with water. The starch substrate was made fresh daily.

Stock iodine solution—Iodine crystals (5.5 g) and potassium iodide (11.0 g) were dissolved in water and were volumetrically diluted to 250 ml. The solution was kept from light.

Dilute iodine solution—Potassium iodide (20 g) and two ml of stock iodine solution were dissolved in water and diluted volumetrically to 500 ml. The solution was made fresh daily.

Enzyme diluting solution—Calcium chloride (11.1 g) was dissolved in four liters of water. Water used for all reagents was either distilled or deionized.

An α-amylase sample was diluted to between 10–15 LU/ml (as defined below) with enzyme diluting solution. For many commercial α-amylase preparations a suitable dilution was found to be 2000 fold. Five milliliter aliquots of dilute iodine solution were dispensed into 13×100 mm test tubes and 10 ml of starch substrate was placed in a 23×200 mm test tube. All tubes were placed in the 30° C. water bath. A Hellige comparator equipped with a special α-amylase color disc (catalog number 620-s5) was used to make readings. Five milliliters of diluted enzyme (also at 30° C.) were mixed with the starch substrate and timing was begun. At appropriate time intervals, for example one minute intervals early in the reaction and 15 second intervals later in the reaction, one ml aliquots of the enzyme-substrate mixture were transferred to a tube containing the dilute iodine solution. The starch iodine solution was mixed and transferred to a 13 mm precision square tube and the color was compared with the standard α-amylase color disc in the Hellige comparator. When the time of the end point was approached, samples were taken at 0.25 minute intervals.

The time required for the colors of the samples and the color disc to match were recorded and the activity (in liquefons per gram or ml) was calculated according to the formula:

$$LU/ml \text{ or } LU/g=$$

Where:

LU=liquefon unit

V=volume of enzyme (5 ml or grams)

t=dextrinization time (minutes)

D=dilution factor:dilution volume divided by ml or g of enzyme diluted.

Mutant α-amylases according to the invention prepared as in Examples 1–4 were tested for their specific activity on starch and soluble substrate. The results, as shown in Table 1, illustrate that mutant amylase according to the invention provides a superior activity in comparison with the wild type α-amylase on both substrates.

TABLE 1

Specific Activity Of Certain α-Amylases On Soluble Substrate And Starch As Percentage Of Wild Type Activity

| α-AMYLASE | Soluble Substrate Assay | Starch Assay |
| --- | --- | --- |
| Wild-type | 100 | 100 |
| M15T/H133Y/N188S/A209V | 140 +/− 12 | 131 +/− 0.5 |
| M15T/H133Y/N188S/A209V/A379S | 143 | 129 +/− 9 |
| M15T/H133Y/N188S/A209V/A379S/G475R | 152 +/− 8 | 175 +/− 12 |

EXAMPLE 6

Starch Liquefaction Results Using Mutant α-Amylase

Starch liquefaction was performed using a reactor composed of 50 feet of 0.24 inch diameter (0.21 inch i.d.) stainless steel tubing bent into an approximately 10 inch diameter coil ~5.5 inches high. The coil was equipped with an 11.5 inch in-line static mixer (Cole-Parmer #G-04669-60)

mounted ~4 feet from the anterior end. The posterior end of the coil was equipped with a Swagelok in-line adjustable pressure relief value (#SS-4CA-3) set at a cracking pressure of about 20 psi. Starch slurry was fed to the coil at a rate of ~70 ml/minute with a piston metering pump. The temperature of the reactor coil was held at 110° C. by immersion of the reactor in a glycerol-water bath. Temperature in the bath was maintained using a circulating heater temperature controller (Fisher Scientific model 7305).

Granular starch was obtained from a corn wet miller and used within two days. The starch was diluted to a desired solids level of about 30–35% dry solids with deionized water and the pH was adjusted with 2.5% NaOH or 6% HCl as required. Calcium was added in the form of $CaCl_2 \cdot 2H_2O$. Typical liquefaction conditions were:

| | |
|---|---|
| Starch | 35% solids |
| Calcium | 20 ppm added, approx. 30 to 40 ppm total, slurry basis |
| pH | 5.0–5.6 |
| α-amylase | 12–28 LU/g of carbohydrate (dry basis) |
| | 9–23 µg/g of carbohydrate (dry basis) |
| SO2 | 50 ppm, slurry basis |
| Primary | 110° C., 5 mins. |
| Secondary | 950° C., 90 mins. |

Samples of starch were transferred from the reactor to a 95° C. second stage liquefaction bath and held for 90 minutes. The degree of starch liquefaction was measured immediately after the second stage liquefaction by determining the dextrose equivalent (DE) of the sample according to the method described in the *Standard Analytical Methods of the Member Companies of the Corn Refiners Association, Inc.*, sixth ed., Analytical Procedure Committee (1980).

α-Amylase comprising the substitutions M15T/H133Y/V148S/N188S/A209V/A379S was compared with a mutant comprising substutions M15T/H133Y/V148S/N188S/A209V/A379S/G475R made as per Examples 1–4 in liquefaction at 110° C in the amount of enzyme required to reach a 10 DE liquefact product. As shown in Table 2, the mutant enzyme according to the invention provided significantly increased performance in jet-liquefaction of starch, especially at low pH over the amylase without a mutation at G475R, specifically, less of the enzyme of the invention is needed to give equal liquefaction at low pH, and at pH 5.6 the mutant enzyme with G475R does not require the addition of exogenous calcium to give equal liquefaction results at the same concentration of enzyme. As a result, less enzyme is needed for equal performance and/or less calcium is needed for equal performance. The amylase dose used in the liquefactions were adjusted so that DE's above and below 10 were obtained at each pH evaluated. The amylase dose (in microgram/gds) required to produce a DE 10 liquefied starch at each pH was then determined by plotting the DE values vs. The amylase dose and interpolating between the data points.

TABLE 2

Amount of Amylase Necessary To Generate A DE 10 Liquefact

| AMYLASE | pH | Amount of Amylase (microgram/gds) |
|---|---|---|
| M15T/H133Y/V148S/N188S/A209V/A379S | 5.0 | 22.15 |
| M15T/H133Y/V148S/N188S/A209V/A379S/G475R | 5.0 | 16.98 |
| M15T/H133Y/V148S/N188S/A209V/A379S | 5.3 | 12.70 |
| M15T/H133Y/V148S/N188S/A209V/A379S/G475R | 5.3 | 10.11 |
| M15T/H133Y/V148S/N188S/A209V/A379S | 5.6 | 8.88 |
| M15T/H133Y/V148S/N188S/A209V/A379S/G475R** | 5.6 | 8.43 |

**liquefaction was at pH 5.6 with no calcium added.

We claim:

1. An α-amylase having a mutation corresponding to G475R in *Bacillus licheniformis*.

2. The α-amylase according to claim 1, wherein said mutation further comprises the deletion or substitution of a methionine or tryptophan residue.

3. The α-amylase according to claim 2, wherein said deletion or substitution of said methionine or tryptophan residue comprises a substitution or deletion corresponding to M15, W138 or M197 in *Bacillus licheniformis*.

4. The α-amylase according to claim 1 wherein said substitution further comprises the deletion or substitution of a residue corresponding to V128, H133, S187 or A209 in *Bacillus licheniformis*.

5. An α-amylase according to claim 1, wherein said substitution comprises a mutation corresponding to M15T/H133Y/S148N/N188S/A209V/A379S/G475R in *Bacillus licheniformis*.

6. The α-amylase according to claim 1, wherein said α-amylase is derived from Bacillus.

7. The α-amylase according to claim 6, wherein said α-amylase is derived from *Bacillus licheniformis*.

8. A DNA encoding the α-amylase according to claim 1.

9. A DNA encoding the α-amylase according to claim 3.

10. A DNA encoding the α-amylase according to claim 4.

11. A DNA encoding the α-amylase according to claim 5.

12. A DNA encoding the α-amylase according to claim 6.

13. An expression vector comprising the DNA of claim 9.

14. A host cell transformed with the expression vector of claim 13.

15. A detergent composition comprising the α-amylase according to claim 1.

16. The detergent composition according to claim 15, wherein said detergent is useful in laundering soiled fabric.

17. The detergent composition according to claim 15, wherein said detergent is useful in washing soiled dishes.

* * * * *

UNITED STATES PATENT AND TRADEMARK OFFICE
CERTIFICATE OF CORRECTION

PATENT NO.   : 6,211,134 B1                                          Page 1 of 1
DATED        : April 3, 2001
INVENTOR(S)  : Caldwell, et al.

It is certified that error appears in the above-identified patent and that said Letters Patent is hereby corrected as shown below:

<u>Column (73)</u>
Assignee: delete "Genecor International, Inc." and insert "Genencor International, Inc."

Signed and Sealed this

Twenty-eighth Day of August, 2001

*Attest:*

*Attesting Officer*

NICHOLAS P. GODICI
*Acting Director of the United States Patent and Trademark Office*

SEQUENCE LISTING

<160> NUMBER OF SEQ ID NOS: 41

<210> SEQ ID NO 1
<211> LENGTH: 56
<212> TYPE: DNA
<213> ORGANISM: Artificial Sequence
<220> FEATURE:
<223> OTHER INFORMATION: Description of Artificial Sequence: Synthetic

<400> SEQUENCE: 1
gatcaaaaca taaaaaccg gccttggccc cgccggtttt ttattatttt tgagct        56

<210> SEQ ID NO 2
<211> LENGTH: 48
<212> TYPE: DNA
<213> ORGANISM: Artificial Sequence
<220> FEATURE:
<223> OTHER INFORMATION: Description of Artificial Sequence: Synthetic

<400> SEQUENCE: 2
ttttgtattt tttggccgga accggggcgg ccaaaaaata ataaaaac              48

```
<210> SEQ ID NO 3
<211> LENGTH: 38
<212> TYPE: DNA
<213> ORGANISM: Artificial Sequence
<220> FEATURE:
<223> OTHER INFORMATION: Description of Artificial Sequence: Synthetic

<400> SEQUENCE: 3
cccattaaga ttggccgcct gggccgacat gttgctgg                              38

<210> SEQ ID NO 4
<211> LENGTH: 37
<212> TYPE: DNA
<213> ORGANISM: Artificial Sequence
<220> FEATURE:
<223> OTHER INFORMATION: Description of Artificial Sequence: Synthetic

<400> SEQUENCE: 4
ggattgggaa gtgtcgactg aaaacggcaa ctatgat                               37

<210> SEQ ID NO 5
<211> LENGTH: 37
<212> TYPE: DNA
<213> ORGANISM: Artificial Sequence
<220> FEATURE:
<223> OTHER INFORMATION: Description of Artificial Sequence: Synthetic

<400> SEQUENCE: 5
ggattgggaa gtttccccag aaaatggcaa ctatgat                               37

<210> SEQ ID NO 6
<211> LENGTH: 37
<212> TYPE: DNA
<213> ORGANISM: Artificial Sequence
<220> FEATURE:
<223> OTHER INFORMATION: Description of Artificial Sequence: Synthetic

<400> SEQUENCE: 6
ggattgggaa gtttctagag aaaacggcaa ctatgat                               37

<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence: Synthetic

<400> SEQUENCE: 7
ggattgggaa gtttccctcg agaacggcaa ctatgat                               37

<210> SEQ ID NO 8
<211> LENGTH: 37
<212> TYPE: DNA
<213> ORGANISM: Artificial Sequence
<220> FEATURE:
<223> OTHER INFORMATION: Description of Artificial Sequence: Synthetic

<400> SEQUENCE: 8
ggattgggaa gtttcggccg aaaacggcaa ctatgat                               37

<210> SEQ ID NO 9
<211> LENGTH: 37
<212> TYPE: DNA
<213> ORGANISM: Artificial Sequence
<220> FEATURE:
<223> OTHER INFORMATION: Description of Artificial Sequence: Synthetic
```

<400> SEQUENCE: 9
ggattgggaa gtttccggag aaaacggcaa ctatgat                                    37

<210> SEQ ID NO 10
<211> LENGTH: 37
<212> TYPE: DNA
<213> ORGANISM: Artificial Sequence
<220> FEATURE:
<223> OTHER INFORMATION: Description of Artificial Sequence: Synthetic

<400> SEQUENCE: 10
ggattgggaa gttagcgtcg aaaacggcaa ctatgat                                    37

<210> SEQ ID NO 11
<211> LENGTH: 37
<212> TYPE: DNA
<213> ORGANISM: Artificial Sequence
<220> FEATURE:
<223> OTHER INFORMATION: Description of Artificial Sequence: Synthetic

<400> SEQUENCE: 11
ggattgggaa gtttccaagg aaaacggcaa ctatgat                                    37

<210> SEQ ID NO 12
<211> LENGTH: 37
<212> TYPE: DNA
<213> ORGANISM: Artificial Sequence
<220> FEATURE:
<223> OTHER INFORMATION: Description of Artificial Sequence: Synthetic

<400> SEQUENCE: 12
ggattgggaa gtttcccagg aaaatggcaa ctatgat                                    37

<210> SEQ ID NO 13
<211> LENGTH: 37
<212> TYPE: DNA
<213> ORGANISM: Artificial Sequence
<220> FEATURE:
<223> OTHER INFORMATION: Description of Artificial Sequence: Synthetic

<400> SEQUENCE: 13
ggattgggaa gtttctcatg aaaacggcaa ctatgat                                    37

<210> SEQ ID NO 14
<211> LENGTH: 37
<212> TYPE: DNA
<213> ORGANISM: Artificial Sequence
<220> FEATURE:
<223> OTHER INFORMATION: Description of Artificial Sequence: Synthetic

<400> SEQUENCE: 14
ggattgggaa gtttccgaag agaacggcaa ctatgat                                    37

<210> SEQ ID NO 15
<211> LENGTH: 37
<212> TYPE: DNA
<213> ORGANISM: Artificial Sequence
<220> FEATURE:
<223> OTHER INFORMATION: Description of Artificial Sequence: Synthetic

<400> SEQUENCE: 15
ggattgggaa gtttccgagg agaacggcaa ctatgat                                    37

<210> SEQ ID NO 16

```
<211> LENGTH: 37
<212> TYPE: DNA
<213> ORGANISM: Artificial Sequence
<220> FEATURE:
<223> OTHER INFORMATION: Description of Artificial Sequence: Synthetic

<400> SEQUENCE: 16
ggattgggaa gtttcatatg aaaacggcaa ctatgat                              37

<210> SEQ ID NO 17
<211> LENGTH: 37
<212> TYPE: DNA
<213> ORGANISM: Artificial Sequence
<220> FEATURE:
<223> OTHER INFORMATION: Description of Artificial Sequence: Synthetic

<400> SEQUENCE: 17
ggattgggaa gtctcctgcg aaaacggcaa ctatgat                              37

<210> SEQ ID NO 18
<211> LENGTH: 37
<212> TYPE: DNA
<213> ORGANISM: Artificial Sequence
<220> FEATURE:
<223> OTHER INFORMATION: Description of Artificial Sequence: Synthetic

<400> SEQUENCE: 18
ggattgggaa gtttccttcg aaaacggcaa ctatgat                              37

<210> SEQ ID NO 19
<211> LENGTH: 37
<212> TYPE: DNA
<213> ORGANISM: Artificial Sequence
<220> FEATURE:
<223> OTHER INFORMATION: Description of Artificial Sequence: Synthetic

<400> SEQUENCE: 19
ggattgggaa gtttcgatcg aaaacggcaa ctatgat                              37

<210> SEQ ID NO 20
<211> LENGTH: 37
<212> TYPE: DNA
<213> ORGANISM: Artificial Sequence
<220> FEATURE:
<223> OTHER INFORMATION: Description of Artificial Sequence: Synthetic

<400> SEQUENCE: 20
ggattgggaa gtttccatgg aaaacggcaa ctatgat                              37

<210> SEQ ID NO 21
<211> LENGTH: 37
<212> TYPE: DNA
<213> ORGANISM: Artificial Sequence
<220> FEATURE:
<223> OTHER INFORMATION: Description of Artificial Sequence: Synthetic

<400> SEQUENCE: 21
ggattgggaa gtttcctggg aaaacggcaa ctatgat                              37

<210> SEQ ID NO 22
<211> LENGTH: 37
<212> TYPE: DNA
<213> ORGANISM: Artificial Sequence
<220> FEATURE:
<223> OTHER INFORMATION: Description of Artificial Sequence: Synthetic

<400> SEQUENCE: 22
```

```
ggattgggaa gtgagctctg aaaacggcaa ctatgat                                    37

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic

<400> SEQUENCE: 23
aggaaaggct tgggattggg aagt                                                  24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic

<400> SEQUENCE: 24
acttcccaat cccaagcctt tcct                                                  24

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic

<400> SEQUENCE: 25
ggcaactatg attatttgat gtat                                                  24

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic

<400> SEQUENCE: 26
atacatcaaa taatcatagt tgcc                                                  24

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 27
cttcattccc gcgacattaa c                                                     21

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 28
gattcccttg tgagaataaa ag                                                    22

<210> SEQ ID NO 29
<211> LENGTH: 24
<212> TYPE: DNA
```

```
<213> ORGANISM: Artificial Sequence
<220> FEATURE:
<223> OTHER INFORMATION: Description of Artificial Sequence: Synthetic

<400> SEQUENCE: 29
aatcatgtca gggaaaaaac tggg                                              24

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic

<400> SEQUENCE: 30
cccagttttt tccctgacat gatt                                              24

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic

<400> SEQUENCE: 31
tttacggtag ctgaatattg gcag                                              24

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic

<400> SEQUENCE: 32
ctgccaatat tcagctaccg taaa                                              24

<210> SEQ ID NO 33
<211> LENGTH: 1968
<212> TYPE: DNA
<213> ORGANISM: Bacillus licheniformis
<220> FEATURE:
<221> NAME/KEY: CDS
<222> LOCATION: (164)..(1699)

<400> SEQUENCE: 33
agcttgaaga agtgaagaag cagagaggct attgaataaa tgagtagaaa gcgccatatc       60
ggcgcttttc ttttggaaga aaatataggg aaaatggtac ttgttaaaaa ttcggaatat      120
ttatacaaca tcatatgttt cacattgaaa ggggaggaga atc atg aaa caa caa       175
                                              Met Lys Gln Gln
                                                1 aaa cgg ctt tac gcc cga ttg ctg acg ctg tta ttt gcg ctc atc ttc       223
Lys Arg Leu Tyr Ala Arg Leu Leu Thr Leu Leu Phe Ala Leu Ile Phe
  5                  10                  15                  20 ttg ctg cct cat tct gca gca gcg gcg gca aat ctt aat ggg acg ctg       271
Leu Leu Pro His Ser Ala Ala Ala Ala Ala Asn Leu Asn Gly Thr Leu
                 25                  30                  35 atg cag tat ttt gaa tgg tac atg ccc aat gac ggc caa cat tgg aag       319
Met Gln Tyr Phe Glu Trp Tyr Met Pro Asn Asp Gly Gln His Trp Lys
             40                  45                  50 cgt ttg caa aac gac tcg gca tat ttg gct gaa cac ggt att act gcc       367
Arg Leu Gln Asn Asp Ser Ala Tyr Leu Ala Glu His Gly Ile Thr Ala
         55                  60                  65
```

-continued

| | | |
|---|---|---|
| gtc tgg att ccc ccg gca tat aag gga acg agc caa gcg gat gtg ggc<br>Val Trp Ile Pro Pro Ala Tyr Lys Gly Thr Ser Gln Ala Asp Val Gly<br>70                            75                        80 | 415 |
| tac ggt gct tac gac ctt tat gat tta ggg gag ttt cat caa aaa ggg<br>Tyr Gly Ala Tyr Asp Leu Tyr Asp Leu Gly Glu Phe His Gln Lys Gly<br>85                            90                        95                      100 | 463 |
| acg gtt cgg aca aag tac ggc aca aaa gga gag ctg caa tct gcg atc<br>Thr Val Arg Thr Lys Tyr Gly Thr Lys Gly Glu Leu Gln Ser Ala Ile<br>105                      110                      115 | 511 |
| aaa agt ctt cat tcc cgc gac att aac gtt tac ggg gat gtg gtc atc<br>Lys Ser Leu His Ser Arg Asp Ile Asn Val Tyr Gly Asp Val Val Ile<br>120                       125                      130 | 559 |
| aac cac aaa ggc ggc gct gat gcg acc gaa gat gta acc gcg gtt gaa<br>Asn His Lys Gly Gly Ala Asp Ala Thr Glu Asp Val Thr Ala Val Glu<br>135                      140                      145 | 607 |
| gtc gat ccc gct gac cgc aac cgc gta att tca gga gaa cac cta att<br>Val Asp Pro Ala Asp Arg Asn Arg Val Ile Ser Gly Glu His Leu Ile<br>150                       155                      160 | 655 |
| aaa gcc tgg aca cat ttt cat ttt ccg ggg cgc ggc agc aca tac agc<br>Lys Ala Trp Thr His Phe His Phe Pro Gly Arg Gly Ser Thr Tyr Ser<br>165                  170                      175                      180 | 703 |
| gat ttt aaa tgg cat tgg tac cat ttt gac gga acc gat tgg gac gag<br>Asp Phe Lys Trp His Trp Tyr His Phe Asp Gly Thr Asp Trp Asp Glu<br>185                      190                      195 | 751 |
| tcc cga aag ctg aac cgc atc tat aag ttt caa gga aag gct tgg gat<br>Ser Arg Lys Leu Asn Arg Ile Tyr Lys Phe Gln Gly Lys Ala Trp Asp<br>200                      205                      210 | 799 |
| tgg gaa gtt tcc aat gaa aac ggc aac tat gat tat ttg atg tat gcc<br>Trp Glu Val Ser Asn Glu Asn Gly Asn Tyr Asp Tyr Leu Met Tyr Ala<br>215                      220                      225 | 847 |
| gac atc gat tat gac cat cct gat gtc gca gca gaa att aag aga tgg<br>Asp Ile Asp Tyr Asp His Pro Asp Val Ala Ala Glu Ile Lys Arg Trp<br>230                      235                      240 | 895 |
| ggc act tgg tat gcc aat gaa ctg caa ttg gac ggt ttc cgt ctt gat<br>Gly Thr Trp Tyr Ala Asn Glu Leu Gln Leu Asp Gly Phe Arg Leu Asp<br>245                  250                      255                      260 | 943 |
| gct gtc aaa cac att aaa ttt tct ttt ttg cgg gat tgg gtt aat cat<br>Ala Val Lys His Ile Lys Phe Ser Phe Leu Arg Asp Trp Val Asn His<br>265                  270                      275 | 991 |
| gtc agg gaa aaa acg ggg aag gaa atg ttt acg gta gct gaa tat tgg<br>Val Arg Glu Lys Thr Gly Lys Glu Met Phe Thr Val Ala Glu Tyr Trp<br>280                      285                      290 | 1039 |
| cag aat gac ttg ggc gcg ctg gaa aac tat ttg aac aaa aca aat ttt<br>Gln Asn Asp Leu Gly Ala Leu Glu Asn Tyr Leu Asn Lys Thr Asn Phe<br>295                      300                      305 | 1087 |
| aat cat tca gtg ttt gac gtg ccg ctt cat tat cag ttc cat gct gca<br>Asn His Ser Val Phe Asp Val Pro Leu His Tyr Gln Phe His Ala Ala<br>310                      315                      320 | 1135 |
| tcg aca cag gga ggc ggc tat gat atg agg aaa ttg ctg aac ggt acg<br>Ser Thr Gln Gly Gly Gly Tyr Asp Met Arg Lys Leu Leu Asn Gly Thr<br>325                  330                      335                      340 | 1183 |
| gtc gtt tcc aag cat ccg ttg aaa tcg gtt aca ttt gtc gat aac cat<br>Val Val Ser Lys His Pro Leu Lys Ser Val Thr Phe Val Asp Asn His<br>345                  350                      355 | 1231 |
| gat aca cag ccg ggg caa tcg ctt gag tcg act gtc caa aca tgg ttt<br>Asp Thr Gln Pro Gly Gln Ser Leu Glu Ser Thr Val Gln Thr Trp Phe<br>360                      365                      370 | 1279 |
| aag ccg ctt gct tac gct ttt att ctc aca agg gaa tct gga tac cct<br>Lys Pro Leu Ala Tyr Ala Phe Ile Leu Thr Arg Glu Ser Gly Tyr Pro<br>375                      380                      385 | 1327 |

```
cag gtt ttc tac ggg gat atg tac ggg acg aaa gga gac tcc cag cgc    1375
Gln Val Phe Tyr Gly Asp Met Tyr Gly Thr Lys Gly Asp Ser Gln Arg
    390                 395                 400 gaa att cct gcc ttg aaa cac aaa att gaa ccg atc tta aaa gcg aga    1423
Glu Ile Pro Ala Leu Lys His Lys Ile Glu Pro Ile Leu Lys Ala Arg
405                 410                 415                 420 aaa cag tat gcg tac gga gca cag cat gat tat ttc gac cac cat gac    1471
Lys Gln Tyr Ala Tyr Gly Ala Gln His Asp Tyr Phe Asp His His Asp
                425                 430                 435 att gtc ggc tgg aca agg gaa ggc gac agc tcg gtt gca aat tca ggt    1519
Ile Val Gly Trp Thr Arg Glu Gly Asp Ser Ser Val Ala Asn Ser Gly
            440                 445                 450 ttg gcg gca tta ata aca gac gga ccc ggt ggg gca aag cga atg tat    1567
Leu Ala Ala Leu Ile Thr Asp Gly Pro Gly Gly Ala Lys Arg Met Tyr
        455                 460                 465 gtc ggc cgg caa aac gcc ggt gag aca tgg cat gac att acc gga aac    1615
Val Gly Arg Gln Asn Ala Gly Glu Thr Trp His Asp Ile Thr Gly Asn
    470                 475                 480 cgt tcg gag ccg gtt gtc atc aat tcg gaa ggc tgg gga gag ttt cac    1663
Arg Ser Glu Pro Val Val Ile Asn Ser Glu Gly Trp Gly Glu Phe His
485                 490                 495                 500 gta aac ggc ggg tcg gtt tca att tat gtt caa aga tagaagagca         1709
Val Asn Gly Gly Ser Val Ser Ile Tyr Val Gln Arg
                505                 510 gagaggacgg atttcctgaa ggaaatccgt tttttatt tgcccgtctt ataaatttct    1769
ttgattacat tttataatta attttaacaa agtgtcatca gccctcagga aggacttgct  1829
gacagtttga atcgcatagg taaggcgggg atgaaatggc aacgttatct gatgtagcaa  1889
agaaagcaaa tgtgtcgaaa atgacggtat cgcgggtgat caatcatcct gagactgtga  1949
cggatgaatt gaaaaagct                                                1968

<210> SEQ ID NO 34
<211> LENGTH: 512
<212> TYPE: PRT
<213> ORGANISM: Bacillus licheniformis

<400> SEQUENCE: 34

Met Lys Gln Gln Lys Arg Leu Tyr Ala Arg Leu Leu Thr Leu Leu Phe
 1               5                  10                  15

Ala Leu Ile Phe Leu Leu Pro His Ser Ala Ala Ala Ala Ala Asn Leu
                20                  25                  30

Asn Gly Thr Leu Met Gln Tyr Phe Glu Trp Tyr Met Pro Asn Asp Gly
            35                  40                  45

Gln His Trp Lys Arg Leu Gln Asn Asp Ser Ala Tyr Leu Ala Glu His
        50                  55                  60

Gly Ile Thr Ala Val Trp Ile Pro Pro Ala Tyr Lys Gly Thr Ser Gln
 65                  70                  75                  80

Ala Asp Val Gly Tyr Gly Ala Tyr Asp Leu Tyr Asp Leu Gly Glu Phe
                85                  90                  95

His Gln Lys Gly Thr Val Arg Thr Lys Tyr Gly Thr Lys Gly Glu Leu
                100                 105                 110

Gln Ser Ala Ile Lys Ser Leu His Ser Arg Asp Ile Asn Val Tyr Gly
        115                 120                 125

Asp Val Val Ile Asn His Lys Gly Gly Ala Asp Ala Thr Glu Asp Val
    130                 135                 140

Thr Ala Val Glu Val Asp Pro Ala Asp Arg Asn Arg Val Ile Ser Gly
```

```
                145                 150                 155                 160
Glu His Leu Ile Lys Ala Trp Thr His Phe His Pro Gly Arg Gly
                    165                 170                 175
Ser Thr Tyr Ser Asp Phe Lys Trp His Trp Tyr His Phe Asp Gly Thr
                180                 185                 190
Asp Trp Asp Glu Ser Arg Lys Leu Asn Arg Ile Tyr Lys Phe Gln Gly
            195                 200                 205
Lys Ala Trp Asp Trp Glu Val Ser Asn Glu Asn Gly Asn Tyr Asp Tyr
        210                 215                 220
Leu Met Tyr Ala Asp Ile Asp Tyr Asp His Pro Asp Val Ala Ala Glu
225                 230                 235                 240
Ile Lys Arg Trp Gly Thr Trp Tyr Ala Asn Glu Leu Gln Leu Asp Gly
                245                 250                 255
Phe Arg Leu Asp Ala Val Lys His Ile Lys Phe Ser Phe Leu Arg Asp
            260                 265                 270
Trp Val Asn His Val Arg Glu Lys Thr Gly Lys Glu Met Phe Thr Val
        275                 280                 285
Ala Glu Tyr Trp Gln Asn Asp Leu Gly Ala Leu Glu Asn Tyr Leu Asn
    290                 295                 300
Lys Thr Asn Phe Asn His Ser Val Phe Asp Val Pro Leu His Tyr Gln
305                 310                 315                 320
Phe His Ala Ala Ser Thr Gln Gly Gly Gly Tyr Asp Met Arg Lys Leu
                325                 330                 335
Leu Asn Gly Thr Val Val Ser Lys His Pro Leu Lys Ser Val Thr Phe
            340                 345                 350
Val Asp Asn His Asp Thr Gln Pro Gly Gln Ser Leu Glu Ser Thr Val
        355                 360                 365
Gln Thr Trp Phe Lys Pro Leu Ala Tyr Ala Phe Ile Leu Thr Arg Glu
    370                 375                 380
Ser Gly Tyr Pro Gln Val Phe Tyr Gly Asp Met Tyr Gly Thr Lys Gly
385                 390                 395                 400
Asp Ser Gln Arg Glu Ile Pro Ala Leu Lys His Lys Ile Glu Pro Ile
                405                 410                 415
Leu Lys Ala Arg Lys Gln Tyr Ala Tyr Gly Ala Gln His Asp Tyr Phe
            420                 425                 430
Asp His His Asp Ile Val Gly Trp Thr Arg Glu Gly Asp Ser Ser Val
        435                 440                 445
Ala Asn Ser Gly Leu Ala Ala Leu Ile Thr Asp Gly Pro Gly Gly Ala
    450                 455                 460
Lys Arg Met Tyr Val Gly Arg Gln Asn Ala Gly Glu Thr Trp His Asp
465                 470                 475                 480
Ile Thr Gly Asn Arg Ser Glu Pro Val Val Ile Asn Ser Glu Gly Trp
                485                 490                 495
Gly Glu Phe His Val Asn Gly Gly Ser Val Ser Ile Tyr Val Gln Arg
            500                 505                 510

<210> SEQ ID NO 35
<211> LENGTH: 483
<212> TYPE: PRT
<213> ORGANISM: Bacillus licheniformis

<400> SEQUENCE: 35

Ala Asn Leu Asn Gly Thr Leu Met Gln Tyr Phe Glu Trp Tyr Met Pro
 1               5                  10                  15
```

-continued

```
Asn Asp Gly Gln His Trp Lys Arg Leu Gln Asn Asp Ser Ala Tyr Leu
             20                  25                  30

Ala Glu His Gly Ile Thr Ala Val Trp Ile Pro Pro Ala Tyr Lys Gly
             35                  40                  45

Thr Ser Gln Ala Asp Val Gly Tyr Gly Ala Tyr Asp Leu Tyr Asp Leu
 50                      55                  60

Gly Glu Phe His Gln Lys Gly Thr Val Arg Thr Lys Tyr Gly Thr Lys
 65                      70                  75                  80

Gly Glu Leu Gln Ser Ala Ile Lys Ser Leu His Ser Arg Asp Ile Asn
                 85                  90                  95

Val Tyr Gly Asp Val Val Ile Asn His Lys Gly Gly Ala Asp Ala Thr
                 100                 105                 110

Glu Asp Val Thr Ala Val Glu Val Asp Pro Ala Asp Arg Asn Arg Val
             115                 120                 125

Ile Ser Gly Glu His Leu Ile Lys Ala Trp Thr His Phe His Phe Pro
 130                     135                 140

Gly Arg Gly Ser Thr Tyr Ser Asp Phe Lys Trp His Trp Tyr His Phe
145                      150                 155                 160

Asp Gly Thr Asp Trp Asp Glu Ser Arg Lys Leu Asn Arg Ile Tyr Lys
                 165                 170                 175

Phe Gln Gly Lys Ala Trp Asp Trp Glu Val Ser Asn Glu Asn Gly Asn
             180                 185                 190

Tyr Asp Tyr Leu Met Tyr Ala Asp Ile Asp Tyr Asp His Pro Asp Val
             195                 200                 205

Ala Ala Glu Ile Lys Arg Trp Gly Thr Trp Tyr Ala Asn Glu Leu Gln
 210                     215                 220

Leu Asp Gly Phe Arg Leu Asp Ala Val Lys His Ile Lys Phe Ser Phe
225                      230                 235                 240

Leu Arg Asp Trp Val Asn His Val Arg Glu Lys Thr Gly Lys Glu Met
                 245                 250                 255

Phe Thr Val Ala Glu Tyr Trp Gln Asn Asp Leu Gly Ala Leu Glu Asn
             260                 265                 270

Tyr Leu Asn Lys Thr Asn Phe Asn His Ser Val Phe Asp Val Pro Leu
             275                 280                 285

His Tyr Gln Phe His Ala Ala Ser Thr Gln Gly Gly Gly Tyr Asp Met
 290                     295                 300

Arg Lys Leu Leu Asn Gly Thr Val Val Ser Lys His Pro Leu Lys Ser
305                      310                 315                 320

Val Thr Phe Val Asp Asn His Asp Thr Gln Pro Gly Gln Ser Leu Glu
                 325                 330                 335

Ser Thr Val Gln Thr Trp Phe Lys Pro Leu Ala Tyr Ala Phe Ile Leu
             340                 345                 350

Thr Arg Glu Ser Gly Tyr Pro Gln Val Phe Tyr Gly Asp Met Tyr Gly
             355                 360                 365

Thr Lys Gly Asp Ser Gln Arg Glu Ile Pro Ala Leu Lys His Lys Ile
 370                     375                 380

Glu Pro Ile Leu Lys Ala Arg Lys Gln Tyr Ala Tyr Gly Ala Gln His
385                      390                 395                 400

Asp Tyr Phe Asp His His Asp Ile Val Gly Trp Thr Arg Glu Gly Asp
                 405                 410                 415

Ser Ser Val Ala Asn Ser Gly Leu Ala Ala Leu Ile Thr Asp Gly Pro
             420                 425                 430

Gly Gly Ala Lys Arg Met Tyr Val Gly Arg Gln Asn Ala Gly Glu Thr
```

-continued

```
                   435                 440                 445
Trp His Asp Ile Thr Gly Asn Arg Ser Glu Pro Val Val Ile Asn Ser
        450                 455                 460

Glu Gly Trp Gly Glu Phe His Val Asn Gly Gly Ser Val Ser Ile Tyr
465                 470                 475                 480

Val Gln Arg

<210> SEQ ID NO 36
<211> LENGTH: 511
<212> TYPE: PRT
<213> ORGANISM: Bacillus licheniformis

<400> SEQUENCE: 36

Met Lys Gln Gln Lys Arg Leu Tyr Ala Arg Leu Leu Thr Leu Leu Phe
 1               5                  10                  15

Ala Leu Ile Phe Leu Leu Pro His Ser Ala Ala Ala Ala Asn Leu
                20                  25                  30

Asn Gly Thr Leu Met Gln Tyr Phe Glu Trp Tyr Met Pro Asn Asp Gly
        35                  40                  45

His Trp Lys Arg Leu Gln Asn Asp Ser Ala Tyr Leu Ala Glu His Gly
    50                  55                  60

Ile Thr Ala Val Trp Ile Pro Pro Ala Tyr Lys Gly Thr Ser Gln Ala
65                  70                  75                  80

Asp Val Gly Tyr Gly Ala Tyr Asp Leu Tyr Asp Leu Gly Glu Phe His
                85                  90                  95

Gln Lys Gly Thr Val Arg Thr Lys Tyr Gly Thr Lys Gly Glu Leu Gln
            100                 105                 110

Ser Ala Ile Lys Ser Leu His Ser Arg Asp Ile Asn Val Tyr Gly Asp
        115                 120                 125

Val Val Ile Asn His Lys Gly Gly Ala Asp Ala Thr Glu Asp Val Thr
    130                 135                 140

Ala Val Glu Val Asp Pro Ala Asp Arg Asn Arg Val Ile Ser Gly Glu
145                 150                 155                 160

His Leu Ile Lys Ala Trp Thr His Phe His Phe Pro Gly Arg Gly Ser
                165                 170                 175

Thr Tyr Ser Asp Phe Lys Trp His Trp Tyr His Phe Asp Gly Thr Asp
            180                 185                 190

Trp Asp Glu Ser Arg Lys Leu Asn Arg Ile Tyr Lys Phe Gln Gly Lys
        195                 200                 205

Ala Trp Asp Trp Glu Val Ser Asn Glu Asn Gly Asn Tyr Asp Tyr Leu
    210                 215                 220

Met Tyr Ala Asp Ile Asp Tyr Asp His Pro Asp Val Ala Ala Glu Ile
225                 230                 235                 240

Lys Arg Trp Gly Thr Trp Tyr Ala Asn Glu Leu Gln Leu Asp Gly Phe
                245                 250                 255

Arg Leu Asp Ala Val Lys His Ile Lys Phe Ser Phe Leu Arg Asp Trp
            260                 265                 270

Val Asn His Val Arg Glu Lys Thr Gly Lys Glu Met Phe Thr Val Ala
        275                 280                 285

Glu Tyr Trp Gln Asn Asp Leu Gly Ala Leu Glu Asn Tyr Leu Asn Lys
    290                 295                 300

Thr Asn Phe Asn His Ser Val Phe Asp Val Pro Leu His Tyr Gln Phe
305                 310                 315                 320

His Ala Ala Ser Thr Gln Gly Gly Gly Tyr Asp Met Arg Lys Leu Leu
```

```
                    325                 330                 335
Asn Gly Thr Val Val Ser Lys His Pro Leu Lys Ser Val Thr Phe Val
                340                 345                 350

Asp Asn His Asp Thr Gln Pro Gly Gln Ser Leu Glu Ser Thr Val Gln
                355                 360                 365

Thr Trp Phe Lys Pro Leu Ala Tyr Ala Phe Ile Leu Thr Arg Glu Ser
    370                 375                 380

Gly Tyr Pro Gln Val Phe Tyr Gly Asp Met Tyr Gly Thr Lys Gly Asp
385                 390                 395                 400

Ser Gln Arg Glu Ile Pro Ala Leu Lys His Lys Ile Glu Pro Ile Leu
                405                 410                 415

Lys Ala Arg Lys Gln Tyr Ala Tyr Gly Ala Gln His Asp Tyr Phe Asp
                420                 425                 430

His His Asp Ile Val Gly Trp Thr Arg Glu Gly Asp Ser Ser Val Ala
                435                 440                 445

Asn Ser Gly Leu Ala Ala Leu Ile Thr Asp Gly Pro Gly Gly Ala Lys
                450                 455                 460

Arg Met Tyr Val Gly Arg Gln Asn Ala Gly Glu Thr Trp His Asp Ile
465                 470                 475                 480

Thr Gly Asn Arg Ser Glu Pro Val Val Ile Asn Ser Glu Gly Trp Gly
                485                 490                 495

Glu Phe His Val Asn Gly Gly Ser Val Ser Ile Tyr Val Gln Arg
                500                 505                 510

<210> SEQ ID NO 37
<211> LENGTH: 520
<212> TYPE: PRT
<213> ORGANISM: Bacillus amyloliquefaciens

<400> SEQUENCE: 37

Met Arg Gly Arg Gly Asn Met Ile Gln Lys Arg Lys Arg Thr Val Ser
  1               5                  10                  15

Phe Arg Leu Val Leu Met Cys Thr Leu Leu Phe Val Ser Leu Pro Ile
                20                  25                  30

Thr Lys Thr Ser Ala Val Asn Gly Thr Leu Met Gln Tyr Phe Glu Trp
            35                  40                  45

Tyr Thr Pro Asn Asp Gly Gln His Trp Lys Arg Leu Gln Asn Asp Ala
        50                  55                  60

Glu His Leu Ser Asp Ile Gly Ile Thr Ala Val Trp Ile Pro Pro Ala
 65                  70                  75                  80

Tyr Lys Gly Leu Ser Gln Ser Asp Asn Gly Tyr Gly Pro Tyr Asp Leu
                85                  90                  95

Tyr Asp Leu Gly Glu Phe Gln Gln Lys Gly Thr Val Arg Thr Lys Tyr
                100                 105                 110

Gly Thr Lys Ser Glu Leu Gln Asp Ala Ile Gly Ser Leu His Ser Arg
            115                 120                 125

Asn Val Gln Val Tyr Gly Asp Val Val Leu Asn His Lys Ala Gly Ala
        130                 135                 140

Asp Ala Thr Glu Asp Val Thr Ala Val Glu Val Asn Pro Ala Asn Arg
145                 150                 155                 160

Asn Gln Glu Thr Ser Glu Glu Tyr Gln Ile Lys Ala Trp Thr Asp Phe
                165                 170                 175

Arg Phe Pro Gly Arg Gly Asn Thr Tyr Ser Asp Phe Lys Trp His Trp
            180                 185                 190
```

```
Tyr His Phe Asp Gly Ala Asp Trp Asp Glu Ser Arg Lys Ile Ser Arg
        195                 200                 205

Ile Phe Lys Phe Arg Gly Glu Gly Lys Ala Trp Asp Trp Glu Val Ser
    210                 215                 220

Ser Glu Asn Gly Asn Tyr Asp Tyr Leu Met Tyr Ala Asp Val Asp Tyr
225                 230                 235                 240

Asp His Pro Asp Val Val Ala Glu Thr Lys Lys Trp Gly Ile Trp Tyr
                245                 250                 255

Ala Asn Glu Leu Ser Leu Asp Gly Phe Arg Ile Asp Ala Ala Lys His
            260                 265                 270

Ile Lys Phe Ser Phe Leu Arg Asp Trp Val Gln Ala Val Arg Gln Ala
        275                 280                 285

Thr Gly Lys Glu Met Phe Thr Val Ala Glu Tyr Trp Gln Asn Asn Ala
    290                 295                 300

Gly Lys Leu Glu Asn Tyr Leu Asn Lys Thr Ser Phe Asn Gln Ser Val
305                 310                 315                 320

Phe Asp Val Pro Leu His Phe Asn Leu Gln Ala Ala Ser Ser Gln Gly
                325                 330                 335

Gly Gly Tyr Asp Met Arg Arg Leu Leu Asp Gly Thr Val Val Ser Arg
            340                 345                 350

His Pro Glu Lys Ala Val Thr Phe Val Glu Asn His Asp Thr Gln Pro
        355                 360                 365

Gly Gln Ser Leu Glu Ser Thr Val Gln Thr Trp Phe Lys Pro Leu Ala
    370                 375                 380

Tyr Ala Phe Ile Leu Thr Arg Glu Ser Gly Tyr Pro Gln Val Phe Tyr
385                 390                 395                 400

Gly Asp Met Tyr Gly Thr Lys Gly Thr Ser Pro Lys Glu Ile Pro Ser
                405                 410                 415

Leu Lys Asp Asn Ile Glu Pro Ile Leu Lys Ala Arg Lys Glu Tyr Ala
            420                 425                 430

Tyr Gly Pro Gln His Asp Tyr Ile Asp His Pro Asp Val Ile Gly Trp
        435                 440                 445

Thr Arg Glu Gly Asp Ser Ser Ala Ala Lys Ser Gly Leu Ala Ala Leu
    450                 455                 460

Ile Thr Asp Gly Pro Gly Gly Ser Lys Arg Met Tyr Ala Gly Leu Lys
465                 470                 475                 480

Asn Ala Gly Glu Thr Trp Tyr Asp Ile Thr Gly Asn Arg Ser Asp Thr
                485                 490                 495

Val Lys Ile Gly Ser Asp Gly Trp Gly Glu Phe His Val Asn Asp Gly
            500                 505                 510

Ser Val Ser Ile Tyr Val Gln Lys
        515                 520

<210> SEQ ID NO 38
<211> LENGTH: 548
<212> TYPE: PRT
<213> ORGANISM: Bacillus stearothermophilus

<400> SEQUENCE: 38

Val Leu Thr Phe His Arg Ile Ile Arg Lys Gly Trp Met Phe Leu Leu
  1               5                  10                  15

Ala Phe Leu Leu Thr Ala Ser Leu Phe Cys Pro Thr Gly Arg His Ala
                 20                  25                  30

Lys Ala Ala Ala Pro Phe Asn Gly Thr Met Met Gln Tyr Phe Glu Trp
             35                  40                  45
```

```
Tyr Leu Pro Asp Asp Gly Thr Leu Trp Thr Lys Val Ala Asn Glu Ala
     50                  55                  60

Asn Asn Leu Ser Ser Leu Gly Ile Thr Ala Leu Ser Leu Pro Pro Ala
 65                  70                  75                  80

Tyr Lys Gly Thr Ser Arg Ser Asp Val Gly Tyr Gly Val Tyr Asp Leu
                 85                  90                  95

Tyr Asp Leu Gly Glu Phe Asn Gln Lys Gly Thr Val Arg Thr Lys Tyr
            100                 105                 110

Gly Thr Lys Ala Gln Tyr Leu Gln Ala Ile Gln Ala Ala His Ala Ala
            115                 120                 125

Gly Met Gln Val Tyr Ala Asp Val Val Phe Asp His Lys Gly Gly Ala
        130                 135                 140

Asp Gly Thr Glu Trp Val Asp Ala Val Glu Val Asn Pro Ser Asp Arg
145                 150                 155                 160

Asn Gln Glu Ile Ser Gly Thr Tyr Gln Ile Gln Ala Trp Thr Lys Phe
                165                 170                 175

Asp Phe Pro Gly Arg Gly Asn Thr Tyr Ser Ser Phe Lys Trp Arg Trp
            180                 185                 190

Tyr His Phe Asp Gly Val Asp Trp Asp Glu Ser Arg Lys Leu Ser Arg
        195                 200                 205

Ile Tyr Lys Phe Arg Gly Ile Gly Lys Ala Trp Asp Trp Glu Val Asp
    210                 215                 220

Thr Glu Asn Gly Asn Tyr Asp Tyr Leu Met Tyr Ala Asp Leu Asp Met
225                 230                 235                 240

Asp His Pro Glu Val Val Thr Glu Leu Lys Asn Trp Gly Lys Trp Tyr
            245                 250                 255

Val Asn Thr Thr Asn Ile Asp Gly Phe Arg Leu Asp Gly Leu Lys His
        260                 265                 270

Ile Lys Phe Ser Phe Phe Pro Asp Trp Leu Ser Tyr Val Arg Ser Gln
    275                 280                 285

Thr Gly Lys Pro Leu Phe Thr Val Gly Glu Tyr Trp Ser Tyr Asp Ile
    290                 295                 300

Asn Lys Leu His Asn Tyr Ile Thr Lys Thr Asn Gly Thr Met Ser Leu
305                 310                 315                 320

Phe Asp Ala Pro Leu His Asn Lys Phe Tyr Thr Ala Ser Lys Ser Gly
            325                 330                 335

Gly Ala Phe Asp Met Arg Thr Leu Met Thr Asn Thr Leu Met Lys Asp
        340                 345                 350

Gln Pro Thr Leu Ala Val Thr Phe Val Asp Asn His Asp Thr Asn Pro
    355                 360                 365

Ala Lys Arg Cys Ser His Gly Arg Pro Trp Phe Lys Pro Leu Ala Tyr
    370                 375                 380

Ala Phe Ile Leu Thr Arg Gln Glu Gly Tyr Pro Cys Val Phe Tyr Gly
385                 390                 395                 400

Asp Tyr Tyr Gly Ile Pro Gln Tyr Asn Ile Pro Ser Leu Lys Ser Lys
                405                 410                 415

Ile Asp Pro Leu Leu Ile Ala Arg Arg Asp Tyr Ala Tyr Gly Thr Gln
            420                 425                 430

His Asp Tyr Leu Asp His Ser Asp Ile Ile Gly Trp Thr Arg Glu Gly
        435                 440                 445

Val Thr Glu Lys Pro Gly Ser Gly Leu Ala Ala Leu Ile Thr Asp Gly
    450                 455                 460
```

```
Ala Gly Arg Ser Lys Trp Met Tyr Val Gly Lys Gln His Ala Gly Lys
465                 470                 475                 480

Val Phe Tyr Asp Leu Thr Gly Asn Arg Ser Asp Thr Val Thr Ile Asn
            485                 490                 495

Ser Asp Gly Trp Gly Glu Phe Lys Val Asn Gly Gly Ser Val Ser Val
            500             505                 510

Trp Val Pro Arg Lys Thr Thr Val Ser Thr Ile Ala Arg Pro Ile Thr
            515             520             525

Thr Arg Pro Trp Thr Gly Glu Phe Val Arg Trp His Glu Pro Arg Leu
        530             535             540

Val Ala Trp Pro
545

<210> SEQ ID NO 39
<211> LENGTH: 32
<212> TYPE: PRT
<213> ORGANISM: Bacillus licheniformis

<400> SEQUENCE: 39

Met Lys Gln Gln Lys Arg Leu Thr Ala Arg Leu Leu Thr Leu Leu Phe
1               5                   10                  15

Ala Leu Ile Phe Leu Leu Pro His Ser Ala Ala Ala Ala Ala Asn Leu
                20                  25                  30

<210> SEQ ID NO 40
<211> LENGTH: 33
<212> TYPE: PRT
<213> ORGANISM: Bacillus subtilis

<400> SEQUENCE: 40

Met Arg Ser Lys Thr Leu Trp Ile Ser Leu Leu Phe Ala Leu Thr Leu
1               5                   10                  15

Ile Phe Thr Met Ala Phe Ser Asn Met Ser Ala Gln Ala Ala Gly Lys
                20                  25                  30

Ser

<210> SEQ ID NO 41
<211> LENGTH: 32
<212> TYPE: PRT
<213> ORGANISM: Bacillus licheniformis

<400> SEQUENCE: 41

Met Arg Ser Lys Thr Leu Trp Ile Ser Leu Leu Phe Ala Leu Thr Leu
1               5                   10                  15

Ile Phe Thr Met Ala Phe Ser Asn Met Ser Ala Gln Ala Ala Asn Leu
                20                  25                  30
```